United States Patent [19]
Godwin

[11] Patent Number: 5,821,338
[45] Date of Patent: Oct. 13, 1998

[54] ANTIBODIES SPECIFIC FOR OVCA DNA ENCODED PROTEINS AND METHODS FOR THEIR USE

[75] Inventor: Andrew K. Godwin, Philadelphia, Pa.

[73] Assignee: Fox Chase Cancer Center, Philadelphia, Pa.

[21] Appl. No.: 493,754

[22] Filed: Jun. 22, 1995

Related U.S. Application Data

[63] Continuation-in-part of Ser. No. 399,986, Mar. 6, 1995.
[51] Int. Cl.$^6$ ..................................................... C07K 16/18
[52] U.S. Cl. ..................................... 530/387.7; 530/387.9; 530/388.2; 530/388.8; 530/389.7
[58] Field of Search .............................. 530/387.7, 387.9, 530/388.5, 389.7, 377.2, 388.8

[56] References Cited

PUBLICATIONS

Foulkes Int. J.Cancer 54: 220–225, 1993.
Nakamura, Nucleic Acid Res. 16:782 1988.
Schultz, Am. J. Hum. Genet. 57(4 Suppl):A4 1995.

*Primary Examiner*—Aoni R. Scheiner
*Assistant Examiner*—Nancy A. Johnson
*Attorney, Agent, or Firm*—Dann, Dorfman, Herrell and Skillman

[57] ABSTRACT

This invention provides a novel gene, OVCA1, isolated from human chromosome 17p13.3. Disruption of the OVCA1 gene is associated with cellular proliferation and tumor development. The OVCA1 gene, along with its encoded protein and antibodies thereto, provides a biological marker for early diagnosis of metastatic disease. The gene also will be useful in gene replacement therapy for treating various forms of cancer.

2 Claims, 9 Drawing Sheets

```
                          MetArg ArgGlnValMet AlaAlaLeuVal ValSerGlyAla    14
  1 CTGTCTTTTTAG TACCACATGCGC AGGCAGGTGATG GCGGCGCTGGTC GTATCCGGGGCA        41
-18

15 AlaGluGlnGly GlyArgAspGly ProGlyArgGly ArgAlaProArg GlyArgValAla        34
 42 GCGGAGCAGGGC GGCCGAGACGGG CCTGGCAGAGGT CGGGCCCCTCGG GGCCGCGTGGCC       101

35 AsnGlnIlePro ProGluIleLeu LysAsnProGln LeuGlnAlaAla IleArgValLeu        54
102 AATCAGATCCCC CCTGAGATCCTG AAGAACCCTCAG CTGCAGGCAGCA ATCCGGGTCCTG       161

55 ProSerAsnTyr AsnPheGluIle ProLysThrIle TrpArgIleGln GlnAlaGlnAla        74
162 CCTTCCAACTAC AACTTTGAGATC CCCAAGACCATC TGGAGGATCCAA CAAGCCCAGGCC       221

75 LysLysValAla LeuGlnMetPro GluGlyLeuLeu LeuPheAlaCys ThrIleValAsp        94
222 AAGAAGGTGGCC TTGCAAATGCCG GAAGGCCTCCTC CTCTTTGCCTGT ACCATTGTGGAT       281

95 IleLeuGluArg PheThrGluAla GluValMetVal MetGlyAspVal ThrTyrGlyAla       114
282 ATCTTGGAAAGG TTCACGGAGGCC GAAGTGATGGTG ATGGGTGACGTG ACCTACGGGGCT       341

115 CysCysValAsp AspPheThrAla ArgAlaLeuGly AlaAspPheLeu ValHisTyrGly       134
342 TGCTGTGTGGAT GACTTCACAGCG AGGGCCCTGGGA GCTGACTTCTTG GTGCACTACGGC       401

135 HisSerCysLeu IleProMetAsp ThrSerAlaGln AspPheArgVal LeuTyrValPhe       154
402 CACAGTTGCCTG ATTCCCATGGAC ACCTCGGCCCAA GACTTCCGGGTG CTGTACGTCTTT       461

155 ValAspIleArg IleAspThrThr HisLeuLeuAsp SerLeuArgLeu ThrPheProPro       174
462 GTGGACATCCGG ATAGACACTACA CACCTCCTGGAC TCTCTCCGCCTC ACCTTTCCCCCA       521
```

Fig. 2A

```
175  AlaThrAlaLeu AlaLeuValSer ThrIleGlnPhe ValSerThrLeu GlnAlaAlaAla  194
522  GCCACTGCCCTT GCCCTGGTCAGC ACCATTCAGTT GTGTCGACCTTG CAGGCAGCCGCC  581

195  GlnGluLeuLys AlaGluTyrArg ValSerValPro GlnCysLysPro LeuSerProGly  214
582  CAGGAGCTGAAA GCCGAGTATCGT GTGAGTGTCCCA CAGTGCAAGCCC CTGTCCCCTGGA  641

215  GluIleLeuGly CysThrSerPro ArgLeuSerArg GluValGluAla ValValTyrLeu  234
642  GAGATCCTGGGC TGCACATCCCCC CGACTGTCCAGA GAGGTGGAGGCC GTTGTGTATCTT  701

235  GlyAspGlyArg PheHisLeuGlu SerValMetIle AlaAsnProAsn ValProAlaTyr  254
702  GGAGATGGCCGC TTCCATCTGGAG TCTGTCATGATT GCCAACCCCAAT GTCCCCGCTTAC  761

255  ArgTyrAspPro TyrSerLysVal LeuSerArgGlu HisTyrAspHis GlnArgMetGln  274
762  CGGTATGACCCA TATAGCAAAGTC CTATCCAGAGAA CACTATGACCAC CAGCGCATGCAG  821

275  AlaAlaArgGln GluAlaIleAla ThrAlaArgSer AlaLysSerTrp GlyLeuIleLeu  294
822  GCTGCTCGCCAA GAAGCCATAGCC ACTGCCCGCTCA GCTAAGTCCTGG GGCCTTATTCTG  881

295  GlyThrLeuGly ArgGlnGlySer ProLysProLeu GluHisLeuGlu SerArgLeuArg  314
882  GGCACTTTGGGG CGCCAGGGCAGT CCTAAGATCCTG GAGCACCTGGAA TCTCGACTCCGA  941

315  AlaLeuGlyLeu SerPheValArg LeuLeuLeuSer GluIlePhePro SerLysLeuSer  334
942  GCCTTGGGCCTT TCCTTTGTGAGG CTGCTGCTCTCT GAGATCTTCCCC AGCAAGCTTAGC  1001

335  LeuLeuProGlu ValAspValTrp ValGlnValAla CysProArgLeu SerIleAspTrp  354
1002 CTACTCCCGAG GTGGATGTGTGG GTGCAGGTGGCA TGTCCACGTCTC TCCATTGACTGG  1061

355  GlyThrAlaPhe ProLysProLeu LeuThrProTyr GluAlaAlaVal AlaLeuArgAsp  374
1062 GGCACAGCCTTC CCCAAGCCGCTG CTGACACCCTAT GAGGCGGCCGTG GCTCTGAGGGAC  1121

375  IleSerTrpGln GlnProTyrPro MetAspPheTyr AlaGlyArgSer LeuGlyProTrp  394
1122 ATTTCCTGGCAG CAGCCCTACCCG ATGGACTTCTAC GCTGGCAGATCC TTGGGGCCCTGG  1181
```

Fig. 2B

```
395   ThrValAsnHis GlyGlnAspArg ArgProHisAla ProGlyArgSer AlaArgGlyLys   414
1182  ACGGTGAACCAC GGGCAGGACCGT CGTCCCCACGCC CCGGGTCGGTCC GCGGGGGGAAG   1241

415   ValGlnGluGly SerAlaArgPro ProSerValVal ValCysGluAsp CysSerCysArg   434
1242  GTGCAGGAGGGG TCCGCGCGTCCC CCTTCGGTCGTG GTTTGCGAGGAC TGCAGCTGCAGG   1301

435   AspGluLysVal AlaProValAsp ProTrpThrArg SerArgAlaSer GlySerCysPro   454
1302  GACGAGAAGGTG GCGCCGGTGGAT CCTTGGACGCGC TCCCGGGCCTCA GGGTCCTGCCCT   1361

455   ProGluGluGln ProArgGlyTrp TrpPheSerGlu GlnGluAlaAsp ValPheSerAla   474
1362  CCGGAGGAGCAG CCTCGAGGCTGG TGGTTTTCAGAG CAGGAGGCCGAC GTTTTCTCCGCA   1421

475   LeuGluGluGlu AlaValCysArg GlyLeuGluGlu SerLeuGlyMet ValAlaGlnAla   494
1422  TTGGAAGAGGAA GCCGTCTGCAGG GGCCTGGAGGAA TCACTGGGGATG GTGGCACAGGCA   1481

495   LeuAsnArgLeu GlyProPheAsp GlyLeuLeuGly PheSerGlnGly AlaAlaLeuAla   514
1482  CTGAACAGGCTG GGGCCTTTTGAC GGCCTTCTTGGT TTCAGCCAAGGG GCTGCGCTAGCA   1541

515   AlaLeuValCys ThrLeuGlyGln AlaGlyAspPro ArgPheProLeu ProArgValTyr   534
1542  GCCCTTGTGTGT ACCCTGGGCCAG GCAGGCGATCCC CGCTTCCCCTTA CCACGGGTTTAT   1601
```

Fig. 2C

```
535   ProLeuGlyVal
1602  CCTCTTGGTGTC TAGTTTCTGTCC CCGGGGCATTGG GTTCAAGGAATC CATCCTCCAAAG   1661
1662  GCCCTTGTCATT GCCTTCGCTCCA TGTTTTGGGGA CACTGACAAAGT CATCCCCTCTCA    1721
1722  GGAGAGTGTGCA ACTGGCCAGCCA ATTCCCGGAGC CATCACCCTCAC CCACTCTGGTGG    1781
1782  CCACTTCATTCC AGCAGCTGCACC CCAGCGTCAGGC CTACCTCAAGTT CTTGGACCAGTT   1841
1842  TGCAGAGTGAAA GATCAAGAAATG TCTCTGCTCCTA CATCCAGCTCCT CTAGGGCAGCC    1901
1902  TCCGTCATCCAT GCCCTCCCAGGA CCCTCCACTCAC TGCTGTGAGTGC GCCTCACCAGAA   1961
1962  CCAGTTAAGAGA CAACTATCAATT CTTGAGACCCAA ATTATAAGGGCC CTGCCCTGTACT   2021
2022  GAAGAAAAGGGG AGCACAAGGCCT TAATGGACATTG ACTTGTGAAAAC GCAAACATGAAT   2081
2082  ATGGTTGGAGAG AGGGTGACATGG CCCTGGATTAGG GGAAGGCAGAGG CTGGCACGATGG   2141
2142  TGACTGCCACAT AATAAAGTGGTG ATTTGGATTTTG NAAAAA  2183
```

| | | | | | |
|---|---|---|---|---|---|
| 1 | GNCCATTACC | AATCGCGAAA | CCAGCGACCC | CTGCGGGTCC | TGTGCCTGGC |
| 51 | GGGCTTCCGG | CAGAGCGAGC | GGGGCTTCCG | TGAGAAGACC | GGGGCGCTGA |
| 101 | GGAAGGCGCT | GCGGGTCGCG | CCGAGCTCGT | GTGCCTCAGC | GCCCGCACCC |
| 151 | GGTCCCCGAC | CCCCGGGCC | CCGAGGGCGC | CAGATCAGAC | TTCGGGTCCT |
| 201 | GCCCTCCGGA | GGAGCAGCCT | CGAGGCTGGT | GGTTTTCAGA | GCAGGAGGCC |
| 251 | GACGTTTTCT | CCGCATTGGA | AGAGCCCGCC | GTCTGCAGGG | GCCTGGAGGA |
| 301 | ATCACTGGGG | ATGGTGGCAC | AGGCACTGAA | CAGGCTGGGG | CCTTTTGACG |
| 351 | GCCTTCTTGG | TTTCAGCCAA | GGGGCTGCGC | TAACAATCCC | TTGTGTGTAC |
| 401 | CCTGGGCCAG | GCAGGCGATC | CCCGCTTCCC | CTTACCACGG | GTTTATCCTC |
| 451 | TTGGTGTCTA | GTTTCTGTCC | CCGGGGCATT | GGGTTCAAGG | AATCCATCCT |
| 501 | CCAAAGGCCC | TTGTCATTGC | CTTCGCTCCA | TGTTTTGGG | GACACTGACA |
| 551 | AAGTCATCCC | CTCTCAGGAG | AGTGTGCAAC | TGGCCAGCCA | ATTTCCCGGA |
| 601 | GCCATCACCC | TCACCCACTC | TGGTGGCCAC | TTCATTCCAG | CAGCTGCACC |
| 651 | CCAGCGTCAG | GCCTACCTCA | AGTTCTTGGA | CCAGTTTGCA | GAGTGAAAGA |
| 701 | TCAAGAAATG | TCTCTGCTCC | TACATCCAGC | TCCTCTAGGG | GCAGCCTCCG |
| 751 | TCATCCATGC | CCTCCCAGGA | CCCTCCACTC | ACTGCTGTGA | GTGCGCCTCA |
| 801 | CCAGAACCAG | TTAAGAGACA | ACTATCAATT | CTTGAGACCC | AAATTATAAG |
| 851 | GGCCCTGCCC | TGTACTGAAG | AAAAGGGGAG | CACAAGGCCT | TAATGGACAT |
| 901 | TGACTTGTGA | AAACGCAAAC | ATGAATATGG | TTGGAGAGCC | CTGGATTAGG |
| 951 | AGGGTGACAT | GGGGAAGGCA | GAGGCTGGCA | CGATGGTGAC | TGCCACATAA |
| 1001 | TAAAGTGGTG | ATTTGGATTT | TGNAAAAA | | |

Fig. 5

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 2182 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
ATGCGCAGGC  AGGTGATGGC  GGCGCTGGTC  GTATCCGGGG  CAGCGGAGCA  GGGCGGCCGA      60

GACGGCCCTG  GCAGAGGTCG  GGCCCCTCGG  GGCCGCGTGG  CCAATCAGAT  CCCCCCTGAG     120

ATCCTGAAGA  ACCCTCAGCT  GCAGGCAGCA  ATCCGGGTCC  TGCCTTCCAA  CTACAACTTT     180

GAGATCCCCA  AGACCATCTG  GAGGATCCAA  CAAGCCCAGG  CCAAGAAGGT  GGCCTTGCAA     240

ATGCCGGAAG  GCCTCCTCCT  CTTTGCCTGT  ACCATTGTGG  ATATCTTGGA  AAGGTTCACG     300
```

| | | | | | |
|---|---|---|---|---|---|
|GAGGCCGAAG|TGATGGTGAT|GGGTGACGTG|ACCTACGGGG|CTTGCTGTGT|GGATGACTTC|360|
|ACAGCGAGGG|CCCTGGGAGC|TGACTTCTTG|GTGCACTACG|GCCACAGTTG|CCTGATGCCC|420|
|ATGGACACCT|CGGCCCAAGA|CTTCCGGGTG|CTGTACGTCT|TTGTGGACAT|CCGGATAGAC|480|
|ACTACACACC|TCCTGGACTC|TCTCCGCCTC|ACCTTTCCCC|CAGCCACTGC|CCTTGCCCTG|540|
|GTCAGCACCA|TTCAGTTTGT|GTCGACCTTG|CAGGCAGCCG|CCCAGGAGCT|GAAAGCCGAG|600|
|TATCGTGTGA|GTGTCCCACA|GTGCAAGCCC|CTGTCCCTG|GAGAGATCCT|GGGCTGCACA|660|
|TCCCCCCGAC|TGTCCAGAGA|GGTGGAGGCC|GTTGTGTATC|TTGGAGATGG|CCGCTTCCAT|720|
|CTGGAGTCTG|TCATGATTGC|CAACCCCAAT|GTCCCGCTT|ACCGGTATGA|CCCATATAGC|780|
|AAAGTCCTAT|CCAGAGAACA|CTATGACCAC|CAGCGCATGC|AGGCTGCTCG|CCAAGAAGCC|840|
|ATAGCCACTG|CCCGCTCAGC|TAAGTCCTGG|GGCCTTATTC|TGGGCACTTT|GGGCCGCCAG|900|
|GGCAGTCCTA|AGATCCTGGA|GCACCTGGAA|TCTCGACTCC|GAGCCTTGGG|CCTTTCCTTT|960|
|GTGAGGCTGC|TGCTCTCTGA|GATCTTCCCC|AGCAAGCTTA|GCCTACTTCC|CGAGGTGGAT|1020|
|GTGTGGGTGC|AGGTGGCATG|TCCACGTCTC|TCCATTGACT|GGGGCACAGC|CTTCCCCAAG|1080|
|CCGCTGCTGA|CACCCTATGA|GGCGGCCGTG|GCTCTGAGGG|ACATTTCCTG|GCAGCAGCCC|1140|
|TACCCGATGG|ACTTCTACGC|TGGCAGCTCC|TTGGGGCCCT|GGACGGTGAA|CCACGGCCAG|1200|
|GACCGCCGTC|CCCACGCCCC|GGGCCGGCCC|GCGCGGGGGA|AGGTGCAGGA|GGGGTCCGCG|1260|
|CGTCCCCCTT|CGGCCGTGGC|TTGCGAGGAC|TGCAGCTGCA|GGGACGAGAA|GGTGGCGCCG|1320|
|CTGGCTCCTT|GACGCGCTCC|CGGGCCTCAG|GGTCCTGCCC|TCCGGAGGAG|CAGCCTCGAG|1380|
|GCTGGTGGTT|TTCAGAGCAG|GAGGCCGACG|TTTTCTCCGC|ATTGGAAGAG|CCCGCCGTCT|1440|
|GCAGGGGCCT|GGAGGAATCA|CTGGGGATGG|TGGCACAGGC|ACTGAACAGG|CTGGGGCCTT|1500|
|TTGACGGCCT|TCTTGGTTTC|AGCCAAGGGG|CTGCGCTAGC|AGCCCTTGTG|TGTGCCCTGG|1560|
|GCCAGGCAGG|CGATCCCCGC|TTCCCCTTGC|CACGGTTTAT|CCTCTTGGTG|TCTAGTTTCT|1620|
|GTCCCCGGGG|CATTGGGTTC|AAGGAATCCA|TCCTCCAAAG|GCCCTTGTCA|TTGCCTTCGC|1680|
|TCCATGTTTT|TGGGGACACT|GACAAAGTCA|TCCCTCTCA|GGAGAGTGTG|CAACTGGCCA|1740|
|GCCAATTTCC|CGGAGCCATC|ACCCTCACCC|ACTCTGGTGG|CCACTTCATT|CCAGCAGCTG|1800|
|CACCCCAGCG|TCAGGCCTAC|CTCAAGTTCT|TGGACCAGTT|TGCAGAGTGA|AAGATCAAGA|1860|
|AATGTCTCTG|CTCCTACATC|CAGCTCCTCT|AGGGGCAGCC|TCCGTCATCC|ATGCCCTCCC|1920|
|AGGACCCTCC|ACTCACTGCT|GTGAGTGCGC|CTCACCAGAA|CCAGTTAAGA|GACAACTATC|1980|
|AATTCTTGAG|ACCCAAATTA|TAAGGGCCCT|GCCCTGTACT|GAAGAAAAGG|GGAGCACAAG|2040|
|GCCTTAATGG|ACATTGACTT|GTGAAAACGC|AAACATGAAT|ATGGTTGGAG|AGCCCTGGAT|2100|
|TAGGAGGGTG|ACATGGGGAA|GGCAGAGGCT|GGCACGATGG|TGACTGCCAC|ATAATAAAGT|2160|
|GGTGATTTGG|ATTTTGNAAA|AA| | | |2182|

( 2 ) INFORMATION FOR SEQ ID NO:2:

( i ) SEQUENCE CHARACTERISTICS:
        ( A ) LENGTH: 443 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

| Met | Arg | Arg | Gln | Val | Met | Ala | Ala | Leu | Val | Val | Ser | Gly | Ala | Ala | Glu |
| 1 | | | | 5 | | | | | 10 | | | | | | 15 |

| Gln | Gly | Gly | Arg | Asp | Gly | Pro | Gly | Arg | Gly | Arg | Ala | Pro | Arg | Gly | Arg |
| | | | 20 | | | | | 25 | | | | | 30 | | |

| Val | Ala | Asn | Gln | Ile | Pro | Pro | Glu | Ile | Leu | Lys | Asn | Pro | Gln | Leu | Gln |
| | | | 35 | | | | 40 | | | | | 45 | | | |

| Ala | Ala | Ile | Arg | Val | Leu | Pro | Ser | Asn | Tyr | Asn | Phe | Glu | Ile | Pro | Lys |
| | 50 | | | | | 55 | | | | | 60 | | | | |

| Thr | Ile | Trp | Arg | Ile | Gln | Gln | Ala | Gln | Ala | Lys | Lys | Val | Ala | Leu | Gln |
| 65 | | | | | 70 | | | | | 75 | | | | | 80 |

| Met | Pro | Glu | Gly | Leu | Leu | Leu | Phe | Ala | Cys | Thr | Ile | Val | Asp | Ile | Leu |
| | | | | 85 | | | | | 90 | | | | | 95 | |

| Glu | Arg | Phe | Thr | Glu | Ala | Glu | Val | Met | Val | Met | Gly | Asp | Val | Thr | Tyr |
| | | | 100 | | | | | 105 | | | | | 110 | | |

| Gly | Ala | Cys | Cys | Val | Asp | Asp | Phe | Thr | Ala | Arg | Ala | Leu | Gly | Ala | Asp |
| | | | 115 | | | | 120 | | | | | 125 | | | |

| Phe | Leu | Val | His | Tyr | Gly | His | Ser | Cys | Leu | Met | Pro | Met | Asp | Thr | Ser |
| | | 130 | | | | 135 | | | | | 140 | | | | |

| Ala | Gln | Asp | Phe | Arg | Val | Leu | Tyr | Val | Phe | Val | Asp | Ile | Arg | Ile | Asp |
| 145 | | | | | 150 | | | | | 155 | | | | | 160 |

| Thr | Thr | His | Leu | Leu | Asp | Ser | Leu | Arg | Leu | Thr | Phe | Pro | Pro | Ala | Thr |
| | | | | 165 | | | | | 170 | | | | | 175 | |

| Ala | Leu | Ala | Leu | Val | Ser | Thr | Ile | Gln | Phe | Val | Ser | Thr | Leu | Gln | Ala |
| | | | 180 | | | | | 185 | | | | | 190 | | |

| Ala | Ala | Gln | Glu | Leu | Lys | Ala | Glu | Tyr | Arg | Val | Ser | Val | Pro | Gln | Cys |
| | | 195 | | | | | 200 | | | | | 205 | | | |

| Lys | Pro | Leu | Ser | Pro | Gly | Glu | Ile | Leu | Gly | Cys | Thr | Ser | Pro | Arg | Leu |
| | 210 | | | | | 215 | | | | | 220 | | | | |

| Ser | Arg | Glu | Val | Glu | Ala | Val | Val | Tyr | Leu | Gly | Asp | Gly | Arg | Phe | His |
| 225 | | | | | 230 | | | | | 235 | | | | | 240 |

| Leu | Glu | Ser | Val | Met | Ile | Ala | Asn | Pro | Asn | Val | Pro | Ala | Tyr | Arg | Tyr |
| | | | | 245 | | | | | 250 | | | | | 255 | |

| Asp | Pro | Tyr | Ser | Lys | Val | Leu | Ser | Arg | Glu | His | Tyr | Asp | His | Gln | Arg |
| | | | 260 | | | | | 265 | | | | | 270 | | |

| Met | Gln | Ala | Ala | Arg | Gln | Glu | Ala | Ile | Ala | Thr | Ala | Arg | Ser | Ala | Lys |
| | | 275 | | | | | 280 | | | | | 285 | | | |

| Ser | Trp | Gly | Leu | Ile | Leu | Gly | Thr | Leu | Gly | Arg | Gln | Gly | Ser | Pro | Lys |
| | 290 | | | | | 295 | | | | | 300 | | | | |

| Ile | Leu | Glu | His | Leu | Glu | Ser | Arg | Leu | Arg | Ala | Leu | Gly | Leu | Ser | Phe |
| 305 | | | | | 310 | | | | | 315 | | | | | 320 |

| Val | Arg | Leu | Leu | Leu | Ser | Glu | Ile | Phe | Pro | Ser | Lys | Leu | Ser | Leu | Leu |
| | | | | 325 | | | | | 330 | | | | | 335 | |

| Pro | Glu | Val | Asp | Val | Trp | Val | Gln | Val | Ala | Cys | Pro | Arg | Leu | Ser | Ile |
| | | | 340 | | | | | 345 | | | | | 350 | | |

| Asp | Trp | Gly | Thr | Ala | Phe | Pro | Lys | Pro | Leu | Leu | Thr | Pro | Tyr | Glu | Ala |
| | | 355 | | | | | 360 | | | | | 365 | | | |

| Ala | Val | Ala | Leu | Arg | Asp | Ile | Ser | Trp | Gln | Gln | Pro | Tyr | Pro | Met | Asp |
| | 370 | | | | | 375 | | | | | 380 | | | | |

| Phe | Tyr | Ala | Gly | Ser | Ser | Leu | Gly | Pro | Trp | Thr | Val | Asn | His | Gly | Gln |
| 385 | | | | | 390 | | | | | 395 | | | | | 400 |

| Asp | Arg | Arg | Pro | His | Ala | Pro | Gly | Arg | Pro | Ala | Arg | Gly | Lys | Val | Gln |
| | | | | 405 | | | | | 410 | | | | | 415 | |

| Glu | Gly | Ser | Ala | Arg | Pro | Pro | Ser | Ala | Val | Ala | Cys | Glu | Asp | Cys | Ser |
|-----|-----|-----|-----|-----|-----|-----|-----|-----|-----|-----|-----|-----|-----|-----|-----|
|     |     |     | 420 |     |     |     |     | 425 |     |     |     |     | 430 |     |     |

| Cys | Arg | Asp | Glu | Lys | Val | Ala | Pro | Leu | Ala | Pro |
|-----|-----|-----|-----|-----|-----|-----|-----|-----|-----|-----|
|     |     |     | 435 |     |     |     | 440 |     |     |     |

( 2 ) INFORMATION FOR SEQ ID NO:3:

( i ) SEQUENCE CHARACTERISTICS:
        ( A ) LENGTH: 1016 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

```
ATGGCCGCGC AGCGACCCCT GCGGGTCCTG TGCCTGGCGG GCTTCCGGCA GAGCGAGCGG      60
GGCTTCCGTG AGAAGACCGG GGCGCTGAGG AAGGCGCTGC GGGGTCGCGC CGAGCTCGTG     120
TGCCTCAGCG GCCCGCACCC GGTCCCCGAC CCCCCGGGCC CCGAGGGCGC CAGATCAGAC     180
TTCGGGTCCT GCCCTCCGGA GGAGCAGCCT CGAGGCTGGT GGTTTTCAGA GCAGGAGGCC     240
GACGTTTTCT CCGCATTGGA AGAGCCCGCC GTCTGCAGGG GCCTGGAGGA ATCACTGGGG     300
ATGGTGGCAC AGGCACTGAA CAGGCTGGGG CCTTTTGACG GCCTTCTTGG TTTCAGCCAA     360
GGGGCTGCGC TAGCAGCCCT TGTGTGTGCC CTGGGCCAGG CAGGCGATCC CCGCTTCCCC     420
TTGCCACGGT TTATCCTCTT GGTGTCTAGT TTCTGTCCCC GGGGCATTGG GTTCAAGGAA     480
TCCATCCTCC AAAGGCCCTT GTCATTGCCT TCGCTCCATG TTTTGGGGA CACTGACAAA      540
GTCATCCCCT CTCAGGAGAG TGTGCAACTG GCCAGCCAAT TTCCCGGAGC CATCACCCTC     600
ACCCACTCTG GTGGCCACTT CATTCCAGCA GCTGCACCCC AGCGTCAGGC CTACCTCAAG     660
TTCTTGGACC AGTTTGCAGA GTGAAAGATC AAGAAATGTC TCTGCTCCTA CATCCAGCTC     720
CTCTAGGGGC AGCCTCCGTC ATCCATGCCC TCCAGGACC CTCCACTCAC TGCTGTGAGT      780
GCGCCTCACC AGAACCAGTT AAGAGACAAC TATCAATTCT TGAGACCCAA ATTATAAGGG     840
CCCTGCCCTG TACTGAAGAA AAGGGGAGCA CAAGGCCTTA ATGGACATTG ACTTGTGAAA     900
ACGCAAACAT GAATATGGTT GGAGAGCCCT GGATTAGGAG GGTGACATGG GGAAGGCAGA     960
GGCTGGCACG ATGGTGACTG CCACATAATA AAGTGGTGAT TTGGATTTTG NAAAAA       1016
```

( 2 ) INFORMATION FOR SEQ ID NO:4:

( i ) SEQUENCE CHARACTERISTICS:
        ( A ) LENGTH: 526 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( i v ) ANTI-SENSE: NO ( v i i i ) POSITION IN GENOME:
        ( A ) CHROMOSOME/SEGMENT: IX Cosmid 9150

( x ) SEQUENCE DESCRIPTION: SEQ ID NO:4:

| Met | Ser | Gly | Ser | Thr | Glu | Ser | Lys | Lys | Gln | Pro | Arg | Arg | Arg | Phe | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Gly Arg Lys Ser Gly Asn Ser Asn Asn Asp Lys Leu Thr Thr Val Ala
             20                  25                  30
Glu Asn Gly Asn Glu Ile Ile His Lys Gln Lys Ser Arg Ile Ala Leu
             35                  40                  45
Gly Arg Ser Val Asn His Val Pro Glu Asp Ile Leu Asn Asp Lys Glu
 50                      55                      60
Leu Asn Glu Ala Ile Lys Leu Leu Pro Ser Asn Tyr Asn Phe Glu Ile
 65                  70                  75                  80
His Lys Thr Val Trp Asn Ile Arg Lys Tyr Asn Ala Lys Arg Ile Ala
                 85                  90                  95
Leu Gln Met Pro Glu Gly Leu Leu Ile Tyr Ser Leu Ile Ile Ser Asp
             100                 105                 110
Ile Leu Glu Gln Phe Cys Gly Val Glu Thr Leu Val Met Gly Asp Val
             115                 120                 125
Ser Tyr Gly Ala Cys Cys Ile Asp Asp Phe Thr Ala Arg Ala Leu Asp
         130                 135                 140
Cys Asp Phe Ile Val His Tyr Ala His Ser Cys Leu Val Pro Ile Asp
145                     150                 155                 160
Val Thr Lys Ile Lys Val Leu Tyr Val Phe Val Thr Ile Asn Ile Gln
                 165                 170                 175
Glu Asp His Ile Ile Lys Thr Leu Gln Lys Asn Phe Pro Lys Gly Ser
             180                 185                 190
Arg Ile Ala Thr Phe Gly Thr Ile Gln Phe Asn Pro Ala Val His Ser
         195                 200                 205
Val Arg Asp Lys Leu Leu Asn Asp Glu Glu His Met Leu Tyr Ile Ile
     210                 215                 220
Pro Pro Gln Ile Lys Pro Leu Ser Arg Gly Glu Val Leu Gly Cys Thr
225                     230                 235                 240
Ser Glu Arg Leu Asp Lys Glu Gln Tyr Asp Ala Met Val Phe Ile Gly
                 245                 250                 255
Asp Gly Arg Phe His Leu Glu Ser Ala Met Ile His Asn Pro Glu Ile
         260                 265                 270
Pro Ala Phe Lys Tyr Asp Pro Tyr Asn Arg Lys Phe Thr Arg Glu Gly
         275                 280                 285
Tyr Asp Gln Lys Gln Leu Val Glu Val Arg Ala Glu Ala Ile Glu Val
 290                 295                 300
Ala Arg Lys Gly Lys Val Phe Gly Leu Ile Leu Gly Ala Leu Gly Arg
305                 310                 315                 320
Gln Gly Asn Leu Asn Thr Val Lys Asn Leu Glu Lys Asn Leu Ile Ala
             325                 330                 335
Ala Gly Lys Thr Val Val Lys Ile Ile Leu Ser Glu Val Phe Pro Gln
         340                 345                 350
Lys Leu Ala Met Phe Asp Gln Ile Asp Val Phe Val Gln Val Ala Cys
         355                 360                 365
Pro Arg Leu Ser Ile Asp Trp Tyr Ala Phe Asn Lys Pro Leu Leu Thr
     370                 375                 380
Pro Tyr Glu Ala Ser Val Leu Leu Lys Lys Asp Val Met Phe Ser Glu
385                     390                 395                 400
Lys Tyr Tyr Pro Met Asp Tyr Tyr Glu Ala Ala Lys Gly Tyr Gly Arg
                 405                 410                 415
Gly Glu Thr Pro Lys Glu Ala Ile Glu Met Leu Lys Val Glu Lys Phe
         420                 425                 430
Lys Lys Leu Lys Arg Phe Glu Val Tyr Tyr Cys Leu Lys Asn Ser Phe
     435                 440                 445
```

```
Leu Glu Glu Val Asp Ile Glu Met Lys Tyr Ser Cys Ser Ile Thr Thr
    450             455             460

Ile Lys Ser Asn Gly Ser Ala Ser Leu Leu Met Asn Trp Glu Glu Leu
465             470             475                         480

Thr Pro Gly His Cys Phe Thr Ser Tyr Thr Asn Pro Ile Ala Gly
                485             490             495

Asp Tyr Gly Leu Asn Ala Ser Ala Ile Asp Gly His Thr Glu Glu Leu
            500             505             510

Val Ala Thr His Pro Ala Gly Thr Leu Glu Asn Ala Thr Gln
        515             520             525
```

( 2 ) INFORMATION FOR SEQ ID NO:5:

( i ) SEQUENCE CHARACTERISTICS:
      ( A ) LENGTH: 661 amino acids
      ( B ) TYPE: amino acid
      ( C ) STRANDEDNESS: Not Relevant
      ( D ) TOPOLOGY: Not Relevant ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

```
Met Ile Thr Phe Gln Leu Pro Ser Asn Tyr Thr Phe Glu Val Pro Lys
1               5               10              15

Thr Ile Trp Lys Ile Arg Ser Thr Glu Ser Lys Tyr Val Ala Leu Gln
            20              25              30

Phe Pro Glu Gly Leu Ile Met Tyr Ala Cys Val Ile Ala Asp Ile Leu
        35              40              45

Glu Lys Tyr Thr Gly Cys Asp Thr Val Ile Met Gly Asp Val Thr Tyr
    50              55              60

Gly Ala Cys Cys Val Asp Asp Thr Tyr Ala Lys Ser Met Gly Cys Asp
65              70              75              80

Leu Leu Val His Tyr Gly His Ser Cys Leu Val Pro Ile Gln Asn Thr
            85              90              95

Asp Gly Ile Ala Met Leu Tyr Val Phe Gly Lys Arg Leu Val Val Val
            100             105             110

Ser Thr Val Gln Phe Ile Pro Ser Leu Gln Thr Leu Arg Thr Thr Phe
        115             120             125

Asn Lys Asp Asp Ser Ser Ile Arg Ile Asp Ile Pro Gln Cys Lys Pro
    130             135             140

Leu Ser Pro Gly Glu Val Leu Gly Cys Thr Ser Pro Arg Leu Asp Ala
145             150             155             160

Ser Lys Tyr Asp Ala Ile Val Tyr Leu Gly Asp Gly Arg Phe His Leu
            165             170             175

Glu Ser Ile Met Ile His Asn Pro Glu Ile Glu Ala Phe Gln Tyr Asp
            180             185             190

Pro Tyr Ser Arg Lys Leu Thr Arg Glu Phe Tyr Asp His Asp Leu Met
        195             200             205

Arg Lys Asn Arg Ile Gly Ser Ile Glu Ile Ala Arg Lys Cys Thr Thr
    210             215             220

Phe Gly Leu Ile Gln Gly Thr Leu Gly Arg Gln Gly Asn Leu Lys Val
225             230             235             240

Val Glu Glu Leu Glu Ala Gln Leu Glu Arg Lys Gly Lys Lys Phe Leu
            245             250             255
```

-continued

```
Arg  Val  Leu  Leu  Ser  Glu  Ile  Phe  Pro  Glu  Lys  Leu  Ala  Met  Phe  Pro
               260                      265                      270

Glu  Val  Asp  Cys  Trp  Val  Gln  Val  Ala  Cys  Pro  Arg  Leu  Ser  Ile  Asp
          275                      280                      285

Trp  Gly  Thr  Gln  Phe  Pro  Lys  Pro  Leu  Leu  Tyr  Pro  Phe  Glu  Leu  Ala
     290                      295                      300

Val  Ala  Leu  Asp  Asn  Val  Ser  Phe  Lys  Phe  Arg  Cys  Leu  Gln  Ile  Thr
305                      310                      315                      320

Gly  Gln  Trp  Thr  Ile  Ile  Arg  Met  Ile  Pro  Trp  Val  Leu  Gly  Arg  Ile
                    325                      330                      335

Ile  Met  Lys  Arg  Thr  Val  Arg  Asn  Gly  Arg  Asn  Gly  Asn  Leu  Ile  Leu
               340                      345                      350

Leu  Ser  Lys  Pro  Lys  Ile  His  Ser  Arg  Glu  Leu  Ser  Tyr  Phe  Asn  Glu
               355                      360                      365

Glu  Lys  Ala  Lys  Arg  Ile  Gly  Glu  Arg  Phe  Glu  Gly  Gly  Lys  Leu  Ala
          370                      375                      380

Lys  Lys  Val  His  Lys  Ser  Ile  Glu  Gln  Leu  Lys  Arg  His  Asp  Pro  Asp
385                      390                      395                      400

Trp  Gln  Ile  Ser  Thr  Glu  Pro  Thr  Lys  Tyr  Leu  Leu  Val  Ser  Asn  Ser
                    405                      410                      415

Ser  Ile  Leu  Cys  Gly  Val  Ser  Leu  Glu  Leu  Glu  Glu  Ile  Phe  Leu
               420                      425                      430

Pro  Leu  Asp  Glu  Leu  Ala  Glu  Phe  Ile  Val  Tyr  Pro  Asn  Lys  Arg  Ser
          435                      440                      445

Tyr  Ser  Phe  Val  Gln  Cys  Ser  Ser  Ile  Glu  Lys  Ser  Ile  Gln  Val  Arg
     450                      455                      460

Thr  Glu  Leu  His  Gly  Leu  Ile  Pro  Pro  Ser  Leu  Lys  Asn  Ser  His  Gln
465                      470                      475                      480

Pro  Phe  Ala  Ile  Ser  Tyr  Val  Glu  Asn  Leu  Pro  Glu  Ala  Thr  Lys  Cys
                    485                      490                      495

Glu  Asp  Phe  Arg  Pro  Ala  Asn  Leu  Lys  Ile  Ile  Glu  Glu  Tyr  Val  Ser
               500                      505                      510

Ser  Asp  Leu  Glu  Lys  Glu  Leu  Val  Asp  Leu  Val  Thr  Asn  His  Pro  Ser
          515                      520                      525

Val  Gln  Ser  Leu  Lys  His  Arg  Ala  Val  Val  His  Phe  Gly  His  Val  Phe
     530                      535                      540

Asp  Tyr  Ser  Thr  Asn  Ser  Ala  Ser  Glu  Trp  Lys  Glu  Ala  Asp  Pro  Ile
545                      550                      555                      560

Pro  Pro  Val  Ile  Asn  Ser  Leu  Ile  Asp  Arg  Leu  Ile  Ser  Asp  Lys  Tyr
                    565                      570                      575

Ile  Thr  Glu  Arg  Pro  Asp  Gln  Val  Thr  Ala  Asn  Val  Tyr  Glu  Ser  Gly
               580                      585                      590

His  Gly  Ile  Pro  Ser  His  Tyr  Asp  Thr  His  Ser  Ala  Phe  Asp  Asp  Pro
          595                      600                      605

Ile  Val  Ser  Ile  Ser  Leu  Leu  Asp  Lys  Val  Val  Met  Glu  Phe  Lys  Asp
     610                      615                      620

Gly  Glu  Asn  Ser  Ala  Arg  Ile  Ala  Pro  Val  Leu  Leu  Lys  Ala  Arg  Ser
625                      630                      635                      640

Leu  Cys  Leu  Ile  Gln  Gly  Glu  Ser  Arg  Tyr  Arg  Trp  Lys  His  Gly  Ile
                    645                      650                      655

Val  Asn  Arg  Lys  Tyr
               660
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:6:

CGCCCCTATC TCCTCCTTTA     20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:7:

TGGTCCTGTC CCTAACTTGG     20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:8:

CATCTCAATC TGGCTTCAGC     20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:9:

AACCCCAGCT CAATGATCAC     20

( 2 ) INFORMATION FOR SEQ ID NO:10:

( i ) SEQUENCE CHARACTERISTICS:
        ( A ) LENGTH: 19 base pairs (B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:10:

CTAGCCCTCC ACCTCTCAT                                            19

(2) INFORMATION FOR SEQ ID NO:11:

(i) SEQUENCE CHARACTERISTICS:
    (A) LENGTH: 18 base pairs
    (B) TYPE: nucleic acid
    (C) STRANDEDNESS: single
    (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:11:

AGCCTGGCTC ACCCTCCT                                             18

(2) INFORMATION FOR SEQ ID NO:12:

(i) SEQUENCE CHARACTERISTICS:
    (A) LENGTH: 18 base pairs
    (B) TYPE: nucleic acid
    (C) STRANDEDNESS: single
    (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:12:

AGGGTGGGTC TCTCCTAC                                             18

(2) INFORMATION FOR SEQ ID NO:13:

(i) SEQUENCE CHARACTERISTICS:
    (A) LENGTH: 18 base pairs
    (B) TYPE: nucleic acid
    (C) STRANDEDNESS: single
    (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:13:

ATGGGGAAGA TGAATGTG                                             18

(2) INFORMATION FOR SEQ ID NO:14:

(i) SEQUENCE CHARACTERISTICS:
    (A) LENGTH: 18 base pairs
    (B) TYPE: nucleic acid
    (C) STRANDEDNESS: single
    (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:14:

CCTCTGCTGC TCCTACCT                                           18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:15:

TGTCCACCCT ACAGGAGG                                           18

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:16:

CTCTCCTGCC CCAGCCGTTG G                                       21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:17:

GATGAACCTA AGACTCCCTC C                                       21

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (i v) ANTI-SENSE: YES (x i) SEQUENCE DESCRIPTION: SEQ ID NO:18:

CTTCTGCTGC CCTAAACCAC 20

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: NO (i v) ANTI-SENSE: YES (x i) SEQUENCE DESCRIPTION: SEQ ID NO:19:

AGTGGCAGGG AATCTCACC 19

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: NO (i v) ANTI-SENSE: YES (x i) SEQUENCE DESCRIPTION: SEQ ID NO:20:

CTGAGTCAGG ATCTGTGTGC A 21

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: NO (i v) ANTI-SENSE: YES (x i) SEQUENCE DESCRIPTION: SEQ ID NO:21:

TGTTCCCAGT CACTTCCCTC 20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: NO (i v) ANTI-SENSE: YES (x i) SEQUENCE DESCRIPTION: SEQ ID NO:22:

TAGGCCAGCG GTTCAGCTTT 20

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:23:

CAGCCTTCAA GACGAGCTG 19

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:24:

CACTGTCACG TTCTTCAGCA 20

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:25:

ACCCCACTCC ACTCCAGAC 19

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:26:

ACACTGGCAG ATGTTATTGT CC 22

( 2 ) INFORMATION FOR SEQ ID NO:27:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:27:

CTCCTCCCTC CTGGAAGC 18

( 2 ) INFORMATION FOR SEQ ID NO:28:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:28:

GGAGGGAAAC GCAGGGTC 18

( 2 ) INFORMATION FOR SEQ ID NO:29:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:29:

AGGCGTTCCC ATGACAAC 18

( 2 ) INFORMATION FOR SEQ ID NO:30:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:30:

GAGGCTGGTG GTTTTCAGAG C 21

( 2 ) INFORMATION FOR SEQ ID NO:31:

( i ) SEQUENCE CHARACTERISTICS:
    ( A ) LENGTH: 22 base pairs
    ( B ) TYPE: nucleic acid (C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:31:

GGGACAGAAA CGAGACACCA AG 22

(2) INFORMATION FOR SEQ ID NO:32:

(i) SEQUENCE CHARACTERISTICS:
(A) LENGTH: 21 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:32:

GGGTTTATCC TCTTGGTGTC T 21

(2) INFORMATION FOR SEQ ID NO:33:

(i) SEQUENCE CHARACTERISTICS:
(A) LENGTH: 21 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:33:

CATTTCTTGA TCTTTCACTC T 21

(2) INFORMATION FOR SEQ ID NO:34:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:34:

TGGACCAGTT TGCAGAGTGA 20

(2) INFORMATION FOR SEQ ID NO:35:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

-continued ( i i i ) HYPOTHETICAL: NO ( i v ) ANTI-SENSE: YES ( x i ) SEQUENCE DESCRIPTION: SEQ ID NO:35:

TATCTGGCAG TCACCATCGT 20

ANTIBODIES SPECIFIC FOR OVCA DNA ENCODED PROTEINS AND METHODS FOR THEIR USE

This application is a continuation-in-part of U.S. application Ser. No. 08/399,986, filed Mar. 6, 1995.

Pursuant to 35 U.S.C. §202(c), it is hereby acknowledged that the U.S. Government has certain rights in the invention described herein, which was made in part with funds from the National Institutes of Health.

FIELD OF THE INVENTION

The present invention relates to diagnosis and treatment of neoplastic disease. In particular, this invention provides a novel gene, OVCA1, the disruption of which is associated with cellular proliferation and tumor development. The OVCA1 gene provides a biological marker for early diagnosis of metastatic disease and may be useful in gene replacement therapy for treating various forms of cancer.

BACKGROUND OF THE INVENTION

The molecular basis of cancer has been the subject of a massive research effort over the past several years. Through this effort, it has been discovered that abnormal cellular proliferation results not only from activation of oncogenes, but from disruption of certain genes whose function appears to be important in maintaining normal cell division. As a well-known example, mutations in the p53 tumor suppressor gene are common in human cancer and can be identified in about half of all cases (see Harris, Science 262: 1980–1981, 1993).

Important regulatory genes such as p53 are often identified by mapping rearrangements or deletions of chromosomes that correlate with the occurrence of a particular type of cancer. The molecular genetic basis of breast cancer and ovarian cancer has been elucidated in part in this manner. Although certain oncogenes are amplified and/or over expressed, the inactivation of multiple tumor suppressor genes appears to be important in the etiology of breast and ovarian cancers, as evidenced by observed allelic losses for polymorphic DNA markers on nearly every chromosome arm. Rearrangements or deletions of chromosome 17 are the most frequently observed changes identified in ovarian and breast cancer tumors.

One strategy for locating putative suppressor genes is to survey tumors for high rates of loss of heterozygosity ("LOH"). Combined data from four separate allelotyping studies of ovarian cancers revealed that greater than 30% of the tumors analyzed showed LOH on chromosome 6, 9, 13q, 17, 18q, 19p, 22q and Xp, with the highest LOH rates on 17q (q21, q22-q23), 17p (p13.3, 13.1), 18q (q21.3-qter, distal 2DCC), 6q (q26-q27), 11q (q23.3-qter), and 11p (p13-p15.5), in descending order. 17p, 17q, 6q, 18q and 11p are frequently deleted in breast carcinomas as well, continuing the genetic parallels between the two cancer sites.

Non-random chromosomal deletions and loss of heterozygosity of a segment of the genome are considered indicative of the presence of a tumor suppressor gene in that region. On the basis of these and other studies of breast and ovarian cancer tumors, it has been suggested that multiple loci on chromosome 17 may be important in the etiology of these diseases. Recent studies (Miki et al., Science 266: 66–71, 1994) have resulted in the identification of the BRCA1 gene, which is responsible for a portion of breast cancer and the majority of ovarian cancer cases caused by inherited susceptibility. Initial studies have indicated however that BRCA1 appears to play little or no role in common, non-hereditary forms of breast and ovarian cancer, suggesting that the genetic basis for more than 90% of cancers of the breast and ovary is still unknown (see Futreal et al., Science 266: 120–122, 1994).

Chromosome 17 has a number of additional potential cancer causing genes, including TP53 at 17p13.1 the BRCA1 gene 17q21, and genes nearby, such as prohibitin and NM23 with plausible tumor suppressor characteristics, and the proto-oncogene cERBB2. Mutations inactivating the tumor suppressing potential of the TP53 gene have also been reported in sporadic breast and ovarian cancer. However, two studies reported a high frequency of LOH on 17p in breast tumors possessing wild-type TP53 (Coles et al., Lancet 336: 761–763, 1990; Cornelis et al., Cancer Res. 54: 4200–4206 1994). It has been shown recently that alterations at 17p13.3 may be an important early event in stage 1 ovarian carcinomas and tumors of low malignant potential. In low malignant potential tumors, allelic losses at 17p13.3 were not accompanied by LOH at TP53, suggesting a more distal suppressor gene and that loss of this gene's function is required for early tumorigenesis. This same region shows frequent loss of heterozygosity in breast cancers, small-cell lung cancers, colon cancers, primitive neuroectodermal tumors, carcinoma of the cervix uteri, medulloblastoma, and astrocytoma, suggesting that a tumor suppressor gene(s) residing on chromosome 17p13.3 is involved in the development of many types of cancers.

Ovarian cancer is the fifth leading cause of cancer-related deaths among women in the United States and the most lethal gynecologic malignancy. Furthermore, more than two-thirds of the women with ovarian cancer are diagnosed with advanced disease when existing therapeutic measures are often ineffective. Breast cancer is one of the most common and important diseases affecting women. Survival rates of breast cancer patients are highest among patients with early stage disease confined to the breast without axillary lymph node involvement.

At present, there are no effective presymptomatic clinical signs or biomarkers of susceptibility to ovarian cancer or breast cancer, making early detection a high priority in medical management of the disease. Efforts to discover prognostic indicators have sought correlations between clinical pathological data and various biochemical parameters. Survival of cancer, whether of the breast, ovaries or another target, is increased through recognition of individuals who are at high risk of a disease, as well as early detection, since current therapeutic strategies for early stage disease have a higher cure rate than for diseases at later stages. For this reason, the identification of molecular markers of oncogenesis will assist in early diagnosis as well as prognostic monitoring of ongoing disease. Furthermore, if such molecular markers comprise mutations or deletions of genes essential for maintaining normal cellular division, such genes may also be developed as therapeutic agents to treat malignant disease.

SUMMARY OF THE INVENTION

In accordance with the present invention, a recombinant DNA molecule is provided which comprises a DNA segment from human chromosome 17p13.3. The DNA segment is at least 20 kilobase pairs in length. In a preferred embodiment, the DNA is isolated from human placental DNA and includes locus D17S28 of chromosome 17p13.3. This segment comprises a gene, referred to herein as OVCA1, the disruption of which is associated with malignant cell growth.

As is typical of many eucaryotic genes, the OVCA1 gene is composed of several exons and introns. The exons of the OVCA1 gene form an open reading frame which has a sequence that encodes a 60 kDa polypeptide, about 530–550 amino acids in length. In a preferred embodiment, the open reading frame encodes an amino acid sequence substantially the same as Sequence I.D. No. 2, set forth in FIG. 2. In a particularly preferred embodiment, the open reading frame comprises Sequence I.D. No. 1, also shown in FIG. 2. The recombinant DNA molecule of the invention may further comprise an additional exon having a sequence substantially the same as Sequence I.D. No. 3, shown in FIG. 5.

According to another aspect of the present invention, an isolated nucleic acid molecule is provided, which comprises an open reading frame of a gene located on human chromosome 17p13.3, the gene occupying a segment of that chromosome, at least twenty kilobase pairs in length. In preferred embodiments of the invention, this nucleic acid molecule comprises a cDNA sequence such as: (1) Sequence I.D. No. 1; (2) a sequence hybridizing with part or all of Sequence I.D. No. 1, and encoding a polypeptide substantially the same as part or all of the polypeptide encoded by Sequence I.D. No. 1; and (3) a sequence encoding part or all of a polypeptide having amino acid Sequence I.D. No. 2. oligonucleotides that specifically hybridize with portions of the OVCA1 gene or OVCA1 open reading frame described above are also provided.

According to another aspect of the present invention, a polypeptide is provided that is produced by expression of isolated nucleic acid molecule comprising part or all of an open reading frame of gene located on human chromosome 17p13.3, the gene occupying a segment of the chromosome at least 20 kb pairs in length. In a preferred embodiment, this polypeptide comprises an amino acid sequence substantially the same as part or all of sequence I.D. No. 2.

According to another aspect of the present invention, antibodies are provided that are immunologically specific for the aforementioned polypeptide or fragments thereof.

The OVCA1 gene, along with its encoded protein and antibodies thereto, provide a much-needed molecular marker for oncogenesis that will assist in early diagnosis and prognostic monitoring of malignant disease, particularly breast cancer and ovarian cancer. The gene also will be useful in gene replacement therapy or for the development of other therapeutic agents to treat various forms of malignant disease.

BRIEF DESCRIPTION OF THE DRAWINGS

FIG. 2. Nucleotide (Sequence I.D. No. 1) and predicted amino acid (Sequence I.D. No. 2) sequences for the OVCA1 cDNA and flanking regions. The predicted amino acid sequences are shown above in the three-letter code. Numbers in the left and right margins correspond to the respective nucleotide and amino acid sequences. The OVCA1 amino acid sequence shown begins at the putative NH2-terminal methionine (nucleotide 1) and ends at nucleotide 1613. The underlining of nucleotides 2153–2158 indicates the putative polyadenylation signal. The sequence shown was obtained from cDNA clones fb67-1 and 77-1, and cosmid clone 7-2, which were isolated from a human fetal brain cDNA and a human placental genomic library, respectively.

FIG. 4. Comparison of the predicted amino acid sequence of the OVCA1 protein with the S. cerevisiae chromosome IX cosmid 9150 (Sequence I.D. No. 4) and *Caenorhabditis elegans* cosmid C14B1 (Sequence I.D. No. 5) predicted proteins. Arrows above sequence indicate the approximate position of OVCA1 introns.

FIG. 5. Nucleotide sequence of OVCA2 (Sequence I.D. No. 3).

DETAILED DESCRIPTION OF THE INVENTION

Figure 1:
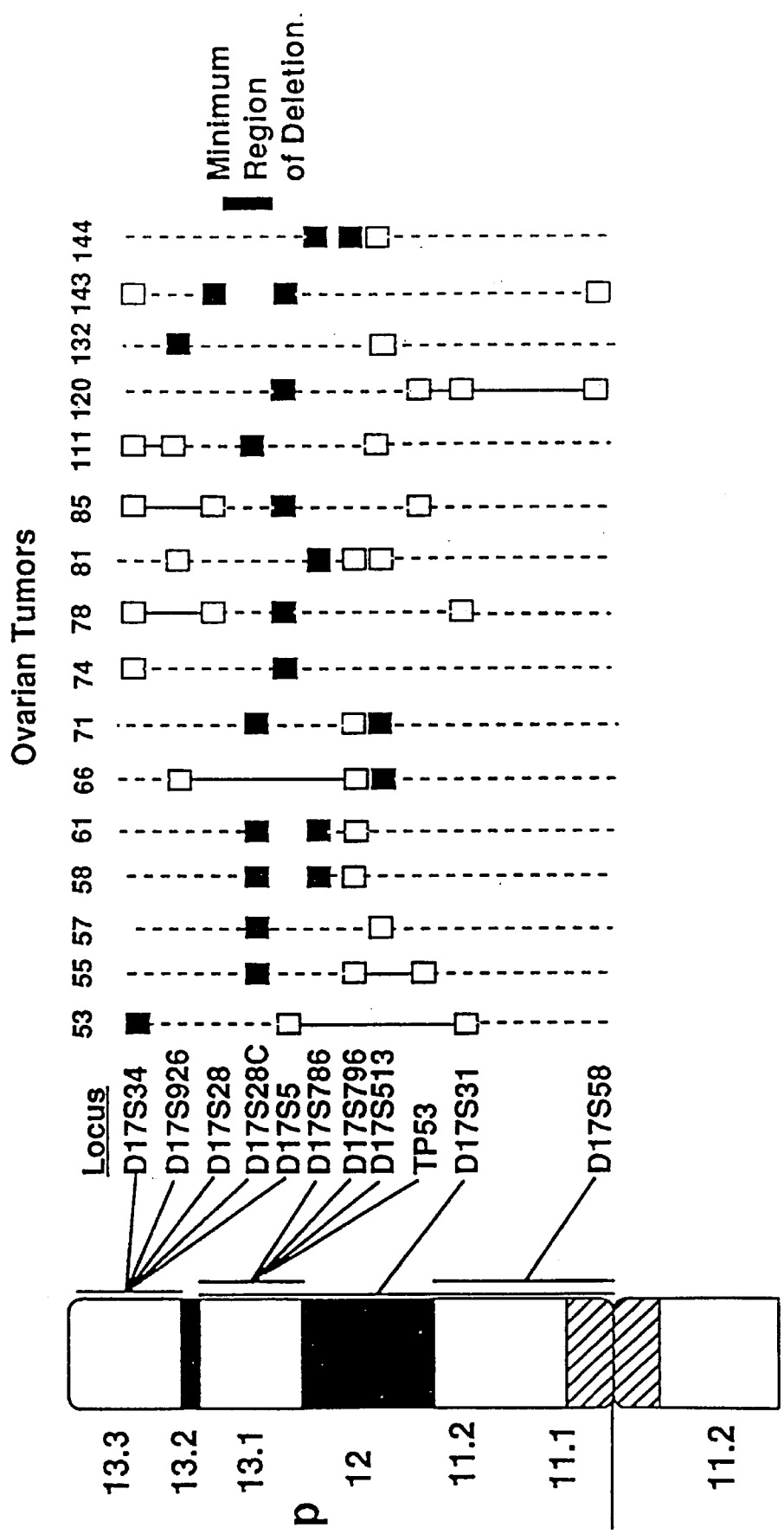
FIG. 1. Allelic deletion patterns of ovarian tumors for the short arm of chromosome 17. DNA samples from normal blood and ovarian tumor tissue were typed with STRPs on 17p. For each tumor, all informative loci are shown. Blackened squares represent constitutional heterozygosity with LOH; open squares, constitutional heterozygosity with no LOH; blank spaces, homozygous. With the assumption that alleles in all regions between loci showing allelic loss are lost, solid lines indicate retained regions of chromosome 17q and open areas show regions of allelic loss. Dashed lines represent regions that are uncertain in tumors with loss of heterozygosity for some loci.

In accordance with the present invention, a new gene from human chromosome 17 has been isolated, which appears to be involved in suppression of tumor development in at least two forms of cancer. This gene, referred to herein as OVCA1 (Ovarian Cancer 1 gene), maps to 17p13.3 and is mutated in a number of tumors and tumor cell lines. Northern blot analysis revealed that a 2.3 kb OVCA1 mRNA is expressed in normal surface epithelial cells of the ovary, but is significantly reduced or is undetectable in 90% (11 of 13) ovarian tumors and tumor cell lines analyzed. Moreover, analysis of fresh ovarian tumors and tumor cell lines has revealed a number of potential cancer-causing mutations in OVCA1 in both tumors and cell lines. These mutations were not detected in patients' matching lymphocyte DNA, suggesting that these alterations resulted from acquired somatic mutations and therefore are not likely to be random polymorphisms. These initial data are consistent with the classification of OVCA1 as a tumor suppressor gene.

The OVCA1 gene spans approximately 20 kb of DNA in chromosome 17p13.3, and is composed of 13 exons. The OVCA1 exons form an open reading frame that encodes a protein of about 538 amino acids with a predicted molecular weight of approximately 60 kDa. The OVCA1 open reading frame (Sequence I.D. No. 1) and corresponding deduced amino acid sequence (Sequence I.D. No. 2) are shown in FIG. 2. In addition, a nucleic acid that represents a unique exon, positioned in the intron between exon 12 and 13 of OVCA1, has been isolated. This sequence (Sequence I.D. No. 3) is referred to as OVCA2 and is shown in FIG. 5.

Sequence comparisons of cDNA clones of OVCA1 and OVCA2 and their predicted proteins (using Genbank/EMBL and Swissplot databases) revealed sequence identity (at the amino acid level) to predicted proteins of unknown function, from *Caenorhabditis elegans* Cosmid c14B1 and the *Saccharomyces cerevisiae* chromosome IX cosmid. High-stringency southern blotting of DNA samples from several different mammalian species with OVCA1 revealed strongly hybridizing fragments in all species examined (see Example 1 for stringency conditions).

The OVCA1 gene having the open reading frame represented by Sequence I.D. No. 1 was isolated by using a number of deletion mapping and positional cloning methods, as described in Example 1. Allelic variants and natural mutants of Sequence I.D. No. 1 (as well as Sequence I.D. Nos. 2 and 3) are likely to exist within the human genome and within genomes of other species. Because such variants are expected to possess certain differences in nucleotide and amino acid sequence, this invention provides an isolated nucleic acid molecule and its encoded protein, having at least about 50–60% (preferably 60–80%, most preferably over 80%) sequence homology in the coding region with the nucleotide sequences set forth as Sequence I.D. No. 1 or No. 3 (and, preferably, specifically comprising the coding region of Sequence I.D. No. 1 or No. 3), and the amino acid sequence of Sequence I.D. No. 2. Because of the natural sequence variation likely to exist among OVCA1 genes and their encoded proteins, one skilled in the art would expect to find up to about 40–50% variation in the coding sequence, while still maintaining the unique properties of the coding sequence and the encoded protein of the present invention. Such an expectation is due in part to the degeneracy of the genetic code, as well as the known evolutionary success of conservative amino acid sequence variations, which do not appreciably alter the nature of a protein. Accordingly, such variants are considered substantially the same as one another and are included within the scope of the present invention. Of course, the introns of the OVCA1 gene are likely to possess even greater sequence variation, in keeping with the known variability of introns in eucaryotic genes.

For purposes of this invention, the term "substantially the same" refers to nucleic acid or amino acid sequences having sequence variations that do not materially affect the nature of the protein (i.e., the structure and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conserved substitute amino acids in the encoded polypeptide. With reference to amino acid sequences, the term "substantially the same" refers generally to conservative substitutions and/or variations in regions of the polypeptide not involved in determination of structure or function.

Persons skilled in the art will appreciate that nucleotide sequences having sufficient homology (as discussed above) to be considered "substantially the same" are often identified by hybridization to one another under appropriate hybridization conditions. Identification and isolation of nucleic acids of the invention by hybridization under various stringency conditions is described in greater detail below.

The following description sets forth the general procedures involved in practicing the present invention. To the extent that specific materials are mentioned, it is merely for purposes of illustration and is not intended to limit the invention. Unless otherwise specified, the general cloning procedures, such as those set forth in Sambrook et al., *Molecular Cloning*, Cold Spring Harbor Laboratory (1989) (hereinafter "Sambrook et al.") are used.

I. Preparation of OVCA1 nucleic acid molecules, encoded proteins and antibodies thereto A. Nucleic Acid Molecules Nucleic acid molecules comprising part or all of the OVCA1 gene of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as Sequence I.D. Nos. 1 and 3, enables preparation of an isolated nucleic acid molecule of the invention by oligonucleotide synthesis. Synthetic oligonucletoides may be prepared by the phosphoramadite method employed in the Applied Biosystems 38A DNA Synthesizer or similar devices. The resultant construct may be purified by high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a double-stranded DNA molecule several kilobases in length may be synthesized as multiple smaller segments of appropriate complementarily. Complementary segments thus produced may be annealed such that each segment possesses appropriate cohesive termini for attachment of an adjacent segment. Adjacent segments may be ligated by annealing cohesive termini in the presence of DNA ligase to construct an entire double-stranded molecule. A synthetic DNA molecule so constructed may then be cloned and amplified in an appropriate vector.

OVCA1 nucleic acid sequences may be isolated from appropriate biological sources using methods known in the art. In a preferred embodiment, a cDNA clone is isolated from an expression library of human origin. In another preferred embodiment, human genomic clones containing OVCA1 may be isolated. Alternatively, cDNA or genomic clones from other species may be obtained.

In accordance with the present invention, nucleic acids having the appropriate sequence homology with part or all of Sequence I.D. Nos. 1 or 3 may be identified by using hybridization and washing condition of appropriate stringency. For example, hybridizations may be performed, according to the method of Sambrook et al., using a hybridization solution comprising: 5×SSC, 5×Denhardt's reagent, 1.0% SDS, 100 $\mu$g/ml denatured, fragmented salmon sperm DNA, 0.05% sodium pyrophosphate and up to 50% formamide. Hybridization is carried out at 37°–42° C. for at least six hour. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42°–65° in 1×SSC and 1% SDS, changing the solution every 30 minutes. In a preferred embodiment, hybridizations are performed in hybridization solution comprising 0.5M NaPO$_4$, 2 mM EDTA, 7% SDS and 0.1% sodium pyrophosphate (pH 7.1) at about 65° C. for 20 hours. For high-stringency conditions, membranes are subsequently washed sequentially for 1 hour each in: (1) 2× SSC, 0.5× SET, 0.1% sodium pyrophosphate; and (2) 0.1× SSC, 0.5× SET, 0.1% sodium pyrophosphate. For low-stringency conditions, membranes are washed at 50° C. for 30 minutes in 2× SSC, 0.5× SET, 0.1% sodium pyrophosphate.

Nucleic acids of the present invention may be maintained as DNA in any convenient cloning vector. In a preferred embodiment, genomic clones are maintained in a cosmid vector, such as pWE15 (Stratagene). In another preferred embodiment, clones are maintained in plasmid cloning/expression vector, such as pBluescript (Stratagene, La Jolla, Calif.), which is propagated in a suitable *E. coli* host cell.

OVCA1 nucleic acid molecules of the invention (including OVCA2) include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of Sequence I.D. Nos. 1 and 3 or selected intron sequences from genomic clones isolated in accordance with the present invention (such as those found in cosmid 7-2, described in Example 1). Such oligonucleotides are useful as probes for detecting OVCA1 genes (and specific mutations) in test samples, e.g. by PCR amplification, or as potential regulators of gene expression.

B. Proteins

A full-length OVCA1-encoded protein of the present invention may be prepared in a variety of ways, according to known methods. The protein may be purified from appropriate sources, e.g., human or animal cultured cells or tissues, by immunoaffinity purification. However, due to the limited amount of such a protein that may be present in a sample at any given time, particularly in tumors or tumor cell lines, conventional purification techniques are not preferred in the present invention.

The availability of the isolated OVCA1 coding sequence enables production of protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wisconsin or BRL, Rockville, Md.

Alternatively, according to a preferred embodiment, the recombinant protein may be produced by expression in a suitable procaryotic or eucaryotic system. For example, part or all of a DNA molecule, such as the cDNA having Sequence I.D. No. 1 or No. 3, may be inserted into a plasmid vector adapted for expression in a bacterial cell, such as *E. coli*, or into a baculovirus vector for expression in an insect cell. Such vectors comprise the regulatory elements necessary for expression of the DNA in the bacterial host cell, positioned in such a manner as to permit expression of the DNA in the host cell. Such regulatory elements required for expression include promoter sequences, transcription initiation sequences and, optionally, enhancer sequences. Production of a recombinant OVCA1 protein by expression in a procaryotic system is described in greater detail in Example 2.

The protein produced by OVCA1 gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

Proteins prepared by the aforementioned methods may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward OVCA1-encoded proteins may be prepared according to standard methods. In a preferred embodiment, monoclonal antibodies are prepared, which react immunospecifically with various epitopes of the proteins. Monoclonal antibodies may be prepared according to general methods of Kohler and Milstein, following standard protocols. Polyclonal or monoclonal antibodies that immunospecifically interact with OVCA1-encoded proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of antibodies are described below.

II. Uses of OVCA1 Nucleic Acids, Encoded Proteins and Antibodies Thereto

As is typical of tumor suppressor genes, rearrangements and mutations in OVCA1 have been found to be associated with the tumorigenic state in tissues and cell lines. Accordingly, isolated OVCA1 nucleic acids, proteins and antibodies thereto will find wide utility as prognostic indicators of neoplastic disease and as therapeutic agents for the treatment of many types of cancer including, but not limited to cancers of the breast, lungs, colon, ovaries and cervix, and other carcinomas such as neuroectodermal tumors, medulloblastoma and astrocytoma.

A. OVCA1 Nucleic Acids

Nucleic acids comprising part or all of the OVCA1 gene may be used for a variety of purposes in accordance with the present invention. As has been done for other tumor suppressor genes, such as p53, selected OVCA1 sequences (DNA, RNA or fragments thereof) may be used as probes to identify mutations or rearrangements in a patient's DNA, and/or monitor the level of OVCA1 transcripts in tissues suspected of being malignant. As discussed earlier, mutations in OVCA1 appear to be associated with sporadic (as opposed to familial) breast cancer as well as with development of ovarian carcinomas, among others. Accordingly, early identification of disruptions in the OVCA1 gene will facilitate diagnosis of malignancies at early stages when the chance for their successful treatment is much greater. OVCA1 sequences may be utilized as probes in a variety of assays known in the art, including but not limited to: (1) in situ hybridization; (2) Southern hybridization; (3) northern hybridization; and (4) assorted amplification reactions, such as polymerase chain reaction (PCR).

The OVCA1 nucleic acids of the invention may also be utilized as probes to identify related genes either from humans or from other species. As discussed above, high-stringency hybridization studies have shown that OVCA1 exists in other mammalian species including but not limited to cow, cat, dog, horse, mouse, pig and rat. As is well known in the art, hybridization stringency may be adjusted so as to allow hybridization of nucleic acid probes with complementary sequencing of varying degrees of homology.

As described above, the coding region of OVCA1 is also used to advantage to produce substantially pure OVCA1 encoded proteins or selected portions thereof. As described below, these proteins may also be used in diagnosis and therapy of metastatic disease.

Because OVCA1 appears to be important in maintenance of normal cell division, a preferred embodiment of the present invention involves gene therapy in which a normal OVCA1 gene or transcript is supplied to a patient having cells or tissues lacking OVCA1, or in which OVCA1 has been disrupted, for the purpose of encouraging normal growth in otherwise tumorigenic tissue. This type of gene therapy may be particularly applicable to cancers of the blood, wherein bone marrow or peripheral blood is subjected to genetic transformation protocols ex vivo, during the course of a normal autologous stem cell transplantation procedure. OVCA1 nucleic acid molecules, or fragments thereof, may also be utilized to control the expression of endogengous OVCA1 genes. If desired, the nucleic acid molecules of the invention may be used to reduce or prevent expression of OVCA1 genes in a targeted cell population. In this embodiment, antisense oligonucleotides are employed which are targeted to specific regions of OVCA1 that are critical for gene expression. The use of antisense oligonucleotides to reduce or eliminate expression of a pre-determined gene is known in the art. In a preferred embodiment, such antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art. This embodiment of the invention may be particularly applicable to the study of cellular proliferation and tumor development in vitro, for the purpose of elucidating the mechanism of cancer development and for developing anti-cancer drugs.

B. OVCA1-Encoded Proteins and Antibodies Thereto

The OVCA1-encoded protein, or fragments thereof, may be used to produce polyclonal or monoclonal antibodies, which also may serve as sensitive detection reagents for the presence and accumulation of the OVCA1-encoded polypeptide in cultured cells or tissues from living patients (the term "patient" refers to both humans and animals). Because the OVCA1-encoded protein has not yet been isolated from natural sources, such antibodies will greatly accelerate the identification, isolation and characterization of this protein in mammalian cells and tissues. Recombinant techniques enable expression of fusion proteins containing part or all of the OVCA1-encoded protein. The full-length protein or fragments of the protein may be used to advantage to generate an array of monoclonal antibodies specific for various epitopes of the protein, thereby potentially providing even greater sensitivity for detection of the protein in cells or tissues.

Polyclonal or monoclonal antibodies immunologically specific for the OVCA1-encoded protein may be used in a variety of assays designed to localize and/or quantitate the protein. Such assays include, but are not limited to: (1) flow cytometric analysis; (2) immunochemical localization of the protein in cultured cells or tissues; and (3) immunoblot analysis (e.g., dot blot, Western blot) of extracts from cells and tissues. Additionally, as described above, such antibodies can be used for the purification of OVCA1-encoded proteins (e.g, affinity column purification, immunoprecipitation).

From the foregoing discussion, it can be seen that OVCA1 nucleic acids, protein and antibodies thereto can be used in many ways for diagnosis and prognosis of human neoplastic diseases. However, one skilled in the art will appreciate that these tools will also be useful in animal and cultured cell experimentation with respect to various carcinomas. They can be used to monitor the effectiveness of potential anti-cancer agents on cellular proliferation in vitro, and/or to assess the development of neoplasms or other malignant diseases in animal model systems.

The following examples are provided to describe the invention in further detail. These examples are intended to illustrate and not to limit the invention.

EXAMPLE 1

Identification of OVCA1, a Candidate Tumor Suppressor Gene on Chromosome 17p13.3

Rearrangements or deletions of chromosome 17 are one of the most frequently observed changes identified in breast and ovarian tumors, among others. Molecular analysis suggests that, in addition to the BRCA1 gene on 17q21 and the TP53 gene on 17p13.1, there is at least one other tumor suppressor gene on chromosome 17 involved in the genesis of ovarian and/or breast cancer. Loss of heterozygosity (LOH) identified within regions of 17p13.3 occurs frequently in ovarian tumors which express wild type TP53. This example describes the use of deletion mapping and positional cloning methods to identify a novel gene, OVCA1 (ovarian cancer 1 gene) that maps to 17p13.3, and is mutated in a number of tumors and tumor cell lines.

MATERIALS AND METHODS

Isolation of DNA and RNA from Tumors and Matched Blood Samples. Preparation of RNA for Northern blotting, and DNA isolation for LOH and SSCP analysis is by methods described in Godwin et al., Am. J. Hum. Genet. 55: 666–677 (1994).

CDNA cloning. Human cDNA libraries derived from an ovarian cancer cell line, A2780, a cervical cancer cell line, HeLa, normal thymus (Stratagene), and fetal brain (Stratagene) were screened by probing with conserved genomic fragments of cosmid 7-2 (described below). Membranes were hybridized at $1.5 \times 10^6$ cpm/ml of hybridization solution (0.5M $NaPO_4$, 2 mM EDTA, 7% SDS, and 0.1% sodium pyrophosphate (NaPPi), 65° C. for 20 hours. The membranes were sequentially washed at high stringency, i.e., 65° C. for 1 hour in 2× SSC, 0.5× SET (1× SET is 1% SDS, 5 mM EDTA, 10 mM Tris-HCl), 0.1% NaPPi; and 0.1× SSC, 0.5× SET, 0.1% NaPPi, respectively. Washed membranes were exposed to Kodak XAR-5 film with a Lightning Plus intensifying screen (NEN-Dupont) at −70° C. DNA probes containing repetitive sequences were pre-annealed using human placental (Sigma, St. Louis, Mo.) and Cot-1 (Bethesda Research Laboratories, Gaithersburg, Md.) DNA prior to hybridization. Positive clones were obtained by screening roughly one million plaques from an oligo (dT)-primed fetal brain cDNA library constructed in pBlue-Script (Stratagene) by hybridization with a 1.6 kbpEcoRI fragment of cosmid 7-2 as probe.

For low-stringency Southern hybridizations, membranes were hybridized as above, but were washed at 50° C. for 30 min. in 2× SSC, 0.5× SET, 0.1% NaPPi. Washed membranes were exposed to Kodak XAR-5 film with a Lightning Plus intensifying screen (NEN-Dupont) at −70° C. DNA probes containing repetitive sequences were pre-annealed using human placental (Sigma, St. Louis, Mo.) and Cot-1 (Bethesda Research Laboratories, Gaithersburg, Md.) DNA prior to hybridization.

Single Strand Conformational Polymorphism (SSCP) Analysis. PCR was carried out in a reaction volume of 10 ml containing 100 ng of genomic DNA template, 10 mM tris-HCl pH 8.3, 50 mM KCl, 1.5 MM $MgCl_2$, 0.001% gelatin, 1 mM each of forward and reverse primer, 60 mM each dATP, dGTP, dCTP, and dTTP, 0.1 mCi [$\alpha$-$^{32}$P]-dATP (DuPont, NEN), 5% dimethyl sulfoxide (DMSO), and 0.5 U Amplitaq DNA polymerase (Perkin Elmer). Following an initial denaturation step at 94° C. for 4 minutes, DNA was amplified through 20 cycles consisting of 1 minute denaturing at 94° C., 1 minute annealing at 68° C.−0.5° C./cycle and 1 minute extension at 72° C. The samples were then subjected to an additional 25 cycles, consisting of 1 minute denaturation at 94° C., 1 minute at 58° C., and 1 minute extension at 72° C., and a final extension at 72° C. for 5 minutes.

PCR reaction products were diluted 1:10 in denaturing loading dye (95% formamide, 10 mM NaOH, 0.25% bromophenol blue, and 0.25% xylene cyanol), heated at 94° C. for 5 minutes, and flash cooled on ice. Four microliters were loaded onto a 0.5×MDE gel (AT Biochem) prepared according to the manufacturer's specifications, and run at 5 watts for 12–16 hours at room temperature in 0.6×TBE (1×= 0.09M Tris, 0.09M boric acid, 0.002M EDTA). Following electrophoresis, the gel was dried and exposed to autoradiography film at −80° C. for 1–12 hours. Variant and normal SSCP bands were cut out from the gels after alignment with the autoradiograph, and the DNA eluted in 100 µl of dd$H_2O$ at 37° C. for 3 hours.

DNA Sequencing. Sequencing was performed on double stranded plasmid DNA using the dideoxy method, with SK, KS or primers derived from obtained sequences (See Table 2). For direct sequencing of the variant SSCP bands, 2 µl of the eluted DNA was used as template for secondary PCR reactions carried out using the conditions described above, except radiolabelled dATP was omitted. Following amplification, the DNA was collected on Wizard resin (Promega), eluted in 50 µl of dd$H_2O$, and the purified PCR product was subjected to cycle sequencing using the fmol DNA Sequencing System (Promega).

PCR analysis of simple tandem repeat polymorphisms. Simple tandem repeat polymorphisms (STRPs) were typed in a PCR based assay containing 15–30 ng of genomic DNA, 10 mM Tris-HCl pH 8.3, 50 mM KCl, 1.5 mM $MgCl_2$, 0.001% gelatin, 0.4 µM of each primer, dCTP, dGTP, and TTP each 16 µM, dATP at 2 µM, 0.65 Ci [$\alpha$-$^{35}$S]-dATP (DuPont, New England Nuclear), 5% DMSO, and 0.25 U Amplitaq DNA polymerase (Perkin Elmer) in a final volume of 5 µl. Alleles were amplified as described above. PCR reaction products were diluted 1:1 in loading buffer (90% formamide, 20 mM ETDA, 0.3% bromophenol blue, 0.3% xylene cyanol), denatured at 94° C. for 5 minutes and loaded (4 µl) onto a 6% denaturing polyacrylamide gel, then electrophoresed at 90 watts in 1×TBE. After electrophoresis, gels were dried at 70° C. under vacuum, and exposed to Kodak XAR 5 film for 24–28 hours.

RESULTS

Interstitial deletions are helpful in defining the smallest region of overlapping deletion in which a tumor suppressor gene may be found. Previous studies have reported that sporadic ovarian tumors of low malignant potential and low-stage carcinomas have allelic loss at chromosome 17p13.3, whereas TP53 at 17p13.1 and the BRCA1 locus at 17q21 are retained. Using DNA isolated from 150 ovarian tumors, a panel of polymorphic DNA markers was evaluated for LOH on 17p. A detailed deletion map of cases showing limited LOH on 17p revealed a common region of deletion, distal to YNH37.3 (D17S28) and proximal to YNZ22 (D17S5), which spans less than 20 kilobase pairs (kbp) and is located on chromosome 17p13.3 (FIG. 1).

Cosmid clones surrounding and including the two loci were isolated from a human placental DNA cosmid library constructed in vector pWE15 (Stratagene). Several strategies were employed to evaluate these clones for potential expressed sequences. First, DNA fragments were evaluated for potential growth suppressor function. We introduced by transfection cosmid clones containing genomic inserts spanning the limited region of deletion and a selectable marker (Neo$^r$) and evaluated clonal outgrowth in the presence of geneticin of the cosmids tested, clone pWE15/7-2, containing approximately 40 kbp of genomic DNA, was the most effective at suppressing colony formation. Cosmid clone pWE15/7-2 was deposited on Nov. 2, 1995 with the American Type Culture Collection and assigned ATCC Accession No. 97331. Next, clone 7-2 was evaluated using exon amplification methods. A 101 bp exon was identified, which mapped to a 1.6 kbp EcoRI DNA fragment of clone 7-2. Hybridization of the 101 bp fragment a low stringency (see Materials and Methods) to a "zoo" blot (see below) revealed conservation among other mammals. Sequencing of the 1.6 kb EcoRI fragment revealed a second potential open reading frame 150 bp away from the putative 101 bp exon.

Four human cDNA libraries, derived from an ovarian cancer cell line, cervical cancer cell line, normal thymus, and fetal brain were screened at high stringency (see Materials and Methods) using the 1.6 kbp EcoRI fragment as a probe. Several positive clones were isolated from the human fetal brain cDNA library constructed in a pBluescript vector (Stratagene). Only two of the clones (fb67-1 and 77-1) hybridized to any of the clones of the 17p13.3 cosmid "contig", indicating the presence of a potential family of genes at loci other than 17p13.3. Related OVCA1 clones isolated from the fetal brain cDNA library were labeled as follows: fb50-1-1, fb52-1-1, fb53-1-1, fb57-1-1, fb63-1-1, fb69-1-1 and fb73-1-1. Partial sequence analysis of these clones has been performed. Other clones that have not been sequenced include fb43-1-1, fb43-2-1 and fb-46-1-1. Because the aforementioned clones were isolated by hybridization with a segment of cosmid clone 7-2 (containing part of Sequence I.D. No. 1), the clones are considered to be "substantially the same" as their corresponding sequences in Sequence I.D. No. 1, within the scope of the present invention.

Sequence analysis of clones fb67-1 and fb77-1 revealed a consensus of 2158 bp (zero bp of the 5'-untranslated, 1589 bp of coding region and 569 bp of the 3'-untranslated region). Identification of a presumptive initation codon flanked by sequences resembling the Kozak consensus sequence was accomplished using an "achored" PCR method (Rapid Amplification of CDNA Ends, Gibco/BRL). Thirty-five additional nucleotides were identified, including 18 bases of the 5'-untranslated region and two potential initation codons. The reading frame using the first AUG encodes a protein of 538 amino acids with a predicted molecular weight of about 60 kDa (FIG. 2). Using the second AUG codon, the predicted protein is about 533 amino acids long with a predicted molecular weight of about 59 kDa. A polyadenylation signal was observed 18 bp upstream from the polyadenylation site (FIG. 2). Northern blot analysis, using the 5'-portion of the fb77-1 cDNA insert as probe, detected a 2.3 kb transcript of RNA from ovarian surface epithelial cells. The length of the cDNA plus 150–200 bp of poly(A) tail probably account for the entire length of the transcript detected in northern blot analysis. A plasmid containing the cDNA molecule encoding OVCA1 has been deposited with the ATCC under the terms of the Budapest Treaty. The plasmid has been given ATCC designation No. 209189.

Genomic DNA samples from several different species were also probed with a full-length OVCA1 cDNA fragment. High stringency blots (see Materials and Methods) revealed strongly hybridizing fragments in tissue from human, cow, cat, dog, horse, mouse, pig, and rat. These results suggest that OVCA1 is highly conserved in mammals.

Figure 4:
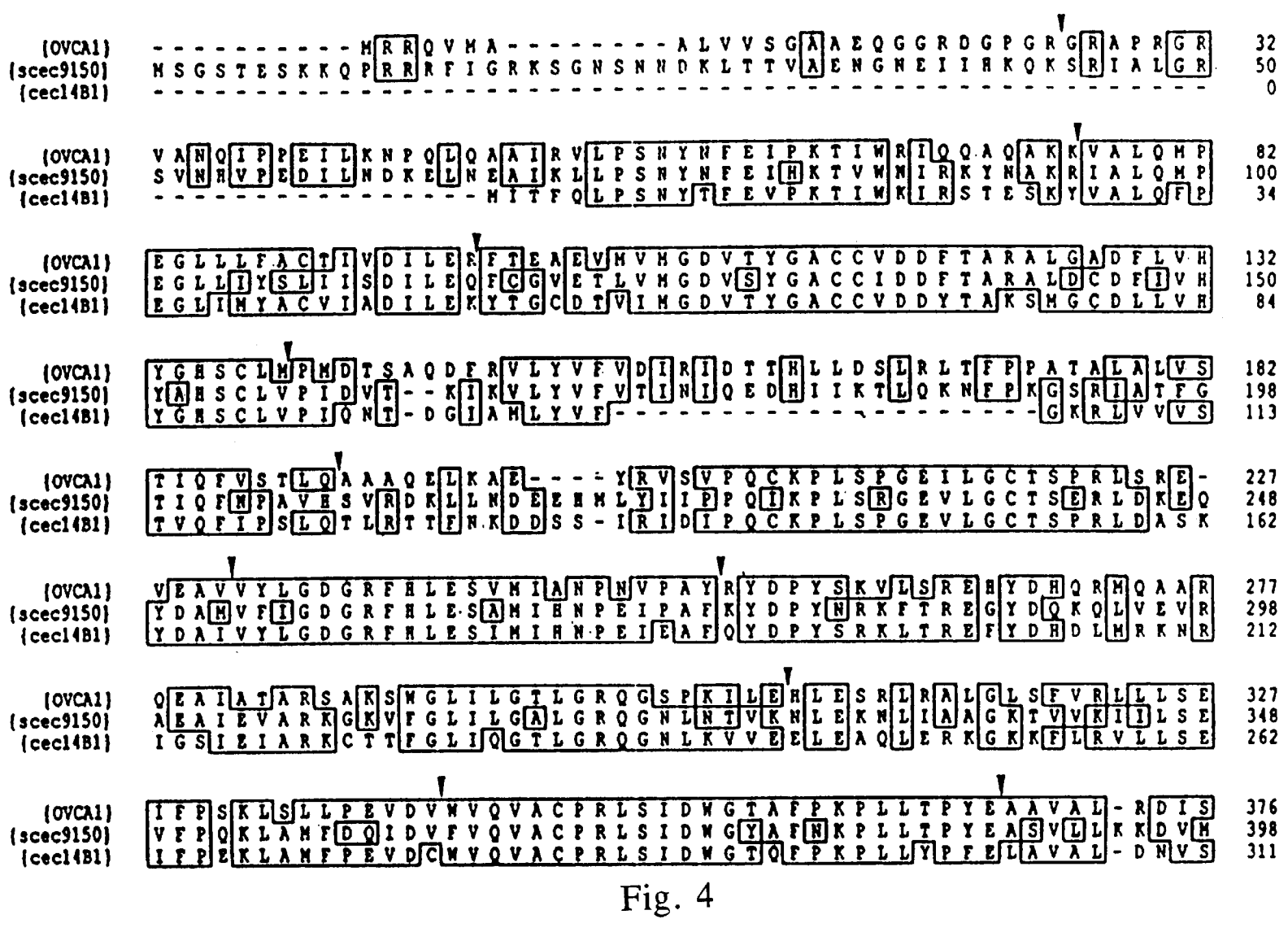
Figure 4:
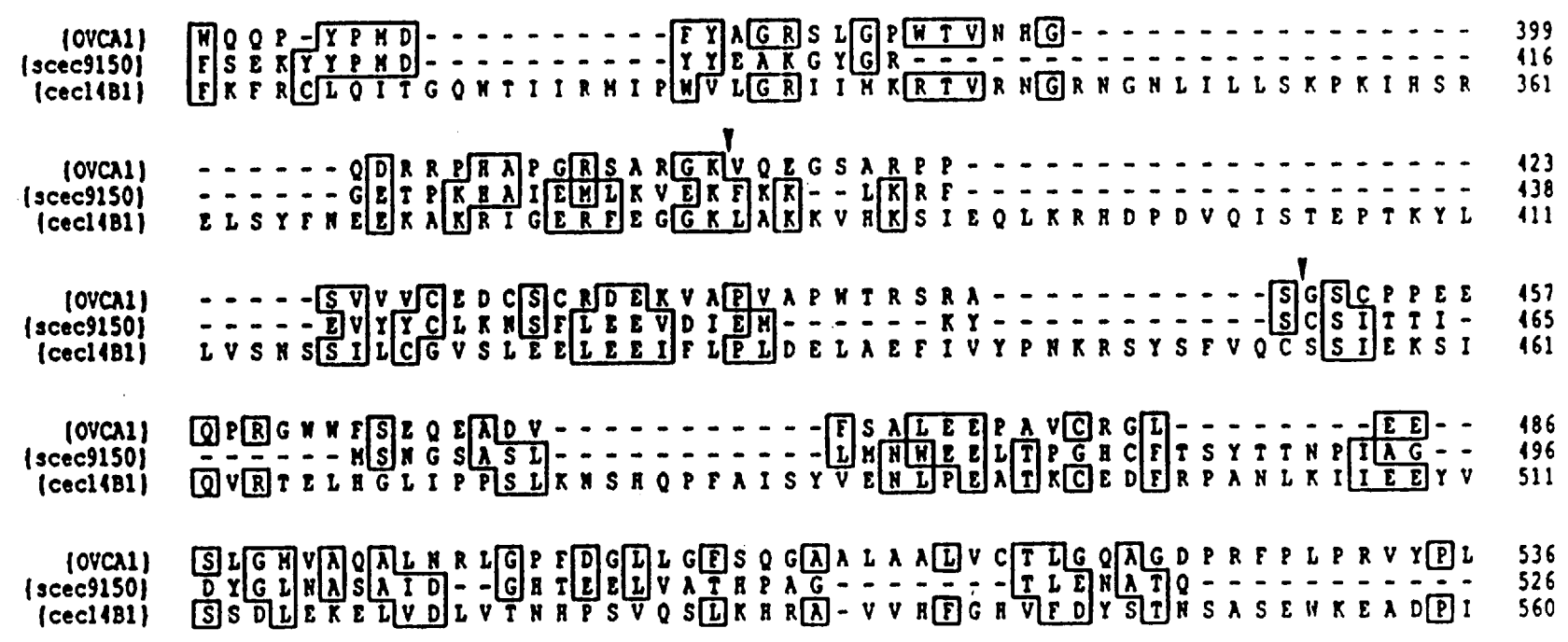

BLAST searches of the Genbank/EMBL and Swissplot databases, respectively, revealed extensive sequence identity (both at the nucleotide or the amino acid level) to two recently identified sequences: S. cerevisiae chromosome IX cosmid 9150 and Caenorhabditis elegans cosmid C14B1 (FIG. 4). The predicted gene product of OVCA1 showed significant sequence similarity over 315 and 375 of the 538 amino acid residues (51% and 44% identity) when compared to the yeast and nematode proteins, respectively. The function of these two predicted proteins is unknown at present time; the sequences were identified as the result of yeast and nematode genome sequencing projects.

Figure 3:
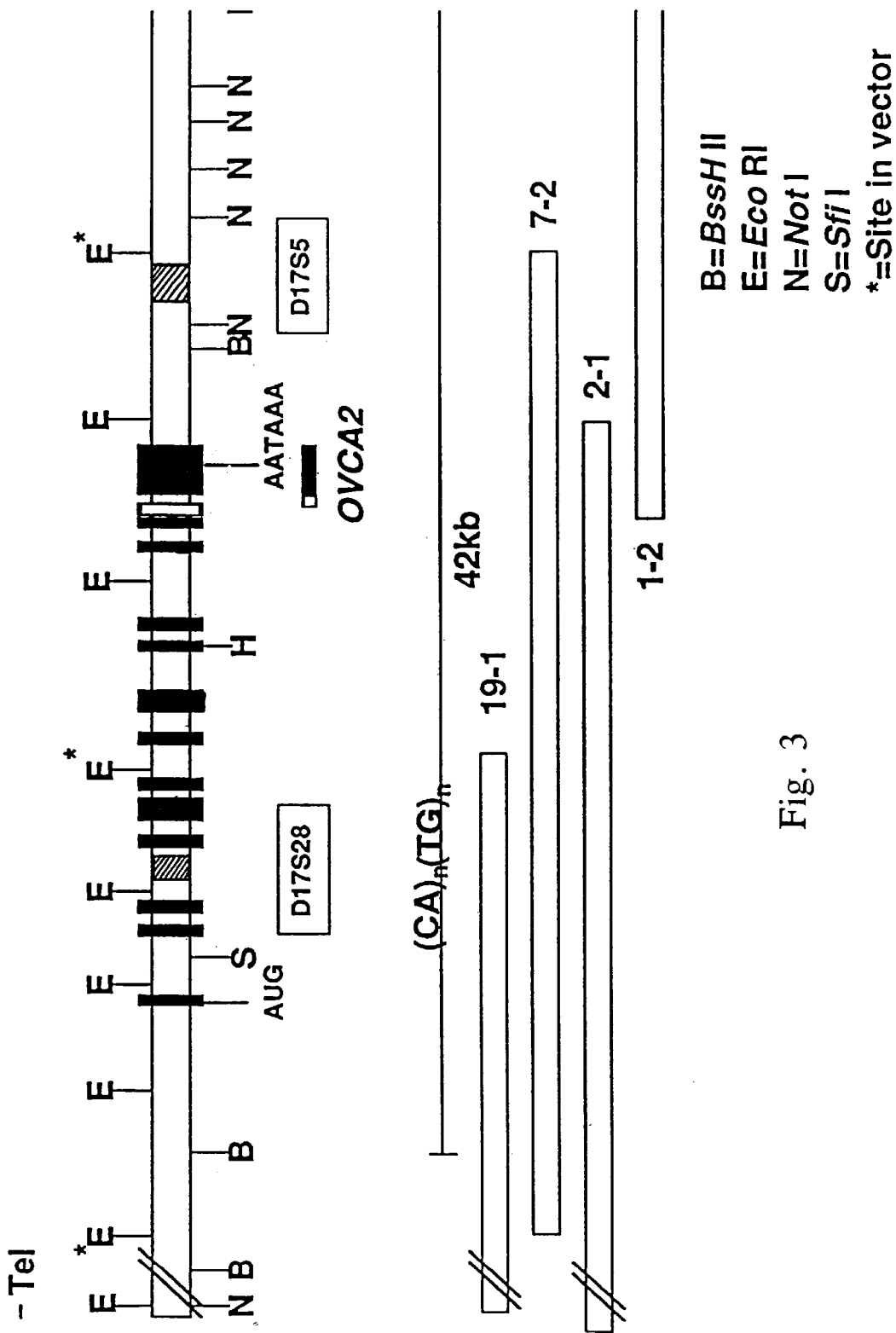
FIG. 3. Schematic diagram of chromosome 17p13.3 containing the OVCA1 gene. Black rectangles correspond to the open reading frames of OVCA1 and white rectangle corresponds to the first exon of OVCA2. Cosmid clones, used to identify OVCA1 and 2, which span the minimal region of deletion in ovarian cancer are indicated. Hatched areas denote locations of loci D17S28 and D17S5.

Restriction mapping of genomic clones using cDNA probes and sequence comparison between cDNA and genomic clones indicated that OVCA1 consists of 13 exons, which span approximately 20 kbp of genomic DNA. The entire OVCA1 cDNA sequence is present in the insert of cosmid 7-2. The position of the 13 exons relative to the common region of deletion defined by DNA markers D17S28 and D17S5 is shown in FIG. 3.

Hybridization of RNA blots to a labeled fragment of the entire fb77-1 cDNA insert revealed two distinct transcripts of 2.3 kb and 1.1 kb. The two transcripts are readily detected in all tissue examined at similar levels. Northern blot analysis reveals that the 2.3 kb OVCA1 mRNA is expressed in normal surface epithelial cells of the ovary, but the level of the 2.3 kb transcript is significantly reduced or is undetectable in a majority (11/13) of the ovarian tumors and tumor cell lines. We have also cloned the smaller transcript and have found that it is composed of exon 13 of OVCA1 and a unique exon positioned in the intron between exon 12 and 13 of OVCA1. We refer to this transcript as OVCA2 (FIG. 5). A plasmid containing the cDNA encoding OVCA2 has been deposited with the ATCC under the terms of the Budapest Treaty. The plasmid has been given ATCC designation No. 209190.

Ovarian carcinomas were typed for LOH, using four highly polymorphic simple tandem repeat markers: D17S926, D17S796 which lie distal to OVCA1 and D17S786, D17S513, which lie proximal to OVCA1. Thirty-seven of 68 (54%) informative ovarian tumors exhibited LOH frequencies consistent with previous measurements. This panel, plus 32 additional ovarian tumors (LOH status undetermined) were examined for OVCA1 mutations. The panel represents Caucasian, Hispanic, and African American patients of varying ages (Table 1).

TABLE 1

Age of ovarian cancer onset and race of patients studied. FCCC, Fox Chase Cancer Center, LH, Lankenau Hospital, GOG, and Gynelogic Oncology Group; Cau, Caucasian, H, Hispanic, Af Am, African American.

|  | AGE | | RACE | | |
|---|---|---|---|---|---|
|  | 45 or under | Over 45 | Cau | H | Af Am |
| FCCC | 5 | 53 | 56 | 0 | 2 |
| LH | 7 | 20 | 22 | 0 | 5 |
| GOG | 15 | 40 | 43 | 5 | 7 |

The complete coding region and intron-exon boundary sequences of OVCA1 was screened in this tumor set by a combination of single-strand conformation polymorphism (SSCP) analysis and direct sequencing. Based on genomic sequence analysis, polymerase chain reaction (PCR) primers were designed to screen the complete coding region (1613) and intron-exon boundaries of OVCA1. Since exon 13 is too large (831 bp) to analyze effectively in one piece by SSCP, three overlapping primer sets were designed for this exon, each with a length of 200–350 bp (Table 2).

TABLE 2

Oligonucleotide primers for OVCA1 (Numbers in parentheses are Sequence I.D. Nos.)

|  | 5'-primer | 3'-primer |
|---|---|---|
| exon1 | CGCCCCTATCTCCTCCTTTA (6) | TGGTCCTGTCCCTAACTTGG (7) |
| exon2 | CATCTCAATCTGGCTTCAGC (8) | AACCCCAGCTCAATGATCAC (9) |
| exon3 | CTAGCCCTCCACCTCTCAT (10) | AGCCTGGCTCACCCTCCT (11) |
| exon4 | AGGGTGGGTCTCTCCTAC (12) | ATGGGGAAGATGAATGTG (13) |
| exon5 | CCTCTGCTGCTCCTACCT (14) | TGTCCACCCTACAGGAGG (15) |
| exon6 | CTCTCCTGCCCCAGCCGTTGG (16) | GATGAACCTAAGACTCCCTCC (17) |
| exon7 | CTTCTGCTGCCCTAAACCAC (18) | AGTGGCAGGGAATCTCACC (19) |
| exon8 | CTGAGTCAGGATCTGTGTGCA (20) | TGTTCCCAGTCACTTCCCTC (21) |
| exon9 | TAGGCCACAGGTTCAGCTTT (22) | CAGCCTTCAAGACGAGCTG (23) |
| exon10 | CACTGTCACGTTCTTCAGCA (24) | ACCCCACTCCACTCCAGAC (25) |
| exon11 | ACACTGGCAGATGTTATTGTCC (26) | CTCCTCCCTCCTGGAAGC (27) |
| exon12 | GGAGGGAAACGCAGGGTC (28) | AGGCGTTCCCATGACAAC (29) |
| exon13a | GAGGCTGGTGGTTTTCAGAGC (30) | GGGACAGAAACTAGACACCAAG (31) |
| exon13b | GGGTTTATCCTCTTGGTGTCT (32) | CATTTCTTGATCTTTCACTCT (33) |
| exon13c | TGGACCAGTTTGCAGAGTGA (34) | TATGTGGCAGTCACCATCGT (35) |

Preliminary studies of 100 fresh ovarian tumors (primarily high grade and late stage) and 13 tumor cell lines for mutations in OVCA1 has revealed a number of potential cancer-causing mutations in both tumors and cell lines (Table 3).

TABLE 3

Mutations in OVCA1.

| Patient # | Location | Codon | Mutation | Result |
|---|---|---|---|---|
| GOG19 | int3 |  | A--G | Unknown |
| OVCAR4 | ex4 | 138 | G--T | Splicing error |
| OVCAR4 | ex4 | 105 | G--C | Met105Ile |

TABLE 3-continued

Mutations in OVCA1.

| Patient # | Location | Codon | Mutation | Result |
|---|---|---|---|---|
| A2780/4E | int4 | | G--A | Splicing error |
| 1A9 | ext4 | 102 | G--A | Ala102Thr |
| GOG4 | int4 | | G--A | Splicing error |
| GOG25 | int4 | | T--A | Splicing error |
| GOG40 | int4 | | C--A | Splicing error |
| UPN61 | ex4 | 99 | C--G | Phe99Leu |
| UPN92 | int4 | | C--G | Unknown |
| UPN106 | ex4 | 105 | A--G | Met105Val |
| UPN123 | ex4 | 105 | A--G | Met105Val |
| CP70 | ex8 | 298 | G--C | Gly298Ala |
| UPN62 | ex9 | 329 | insC | Frameshift |
| UPN96 | ex13 | 563 | G--T | Met563Arg |

A total of fifteen mutations, many in the introns flanking exon 4, have been detected. Moreover, these mutations are not detected in the patients' matching lymphocyte DNA, suggesting that these alterations are the result of acquired somatic mutations and are therefore not likely to be random polymorphisms. Multiple common and rare polymorphisms were also identified in the OVCA1 coding sequence (Table 4) and were used to directly assess the frequency of LOH for OVCA1.

TABLE 4

Polymorphisms in OVCA1

| Exon | Codon Location | Base in Codon | Nucleotide Change | Result |
|---|---|---|---|---|
| 1 | 7 | 2 | C--T | Ala--Val |
| 2 | 32 | 2 | C--A | Ala--Asp |
| 4 | 104 | 3 | G--A | Val--Val |
| 5 | 188 | 3 | G--A | Ser--Ser |
| 5 | N.D. | N.D. | N.D. | N.D. |
| 9 | 336 | 1 | C--G | Leu--Val |
| 9 | 338 | 3 | C--T | Pro--Pro |

EXAMPLE 2

Production of Fusion OVCA1 Proteins

Fragments of the OVCA1 CDNA (Sequence I.D. No. 1) were ligated in the BamHI and EcoRI sites of the pGEX bacterial expression vector (commercially available). When expressed in bacteria, the pGEX vector produces a fusion protein between bacterial glutathione S-tranferase and the desired portions of the OVCA1 protein. *E. coli* cells were transformed with these constructs and the proteins prepared by inducing expression from an overnight culture with 0.1 mM IPTG for 2 hours. The cells were pelleted, washed with phosphate-buffered saline (PBS) and then sonicated. The bacterial debris was pelleted by centrifugation and the supernatant passed over a glutathione-Sepharose column. The protein was eluted using 5 mM glutathione in 50 mM Tris-HCl, pH 8.0. Protein yields have not yet been quantitated or optimized; however, this expression system routinely yields 1 mg of protein from 200 ml of bacterial cells.

The present invention is not limited to the embodiments described and exemplified above, but is capable of variation and modification without departure from the scope of the appended claims.

What is claimed is:

1. An antibody that specifically binds a polypeptide produced by expression of a cDNA molecule present in a plasmid vector, said vector having ATCC designation No. 209189, said cDNA molecule being approximately 2.3 kb in length and reverse transcribed from an mRNA molecule expressed from a DNA sequence present in human chromosome 17p13.3, said DNA sequence including locus D1728, disruption of said DNA sequence being associated with malignant cell growth.

2. An antibody that specifically binds a polypeptide produced by expression of a cDNA molecule present in a plasmid vector, said vector having ATCC desination No. 209190, sand cDNA molecule being approximately 1.1 kb in length and reverse transcribed froma mRNA molecule expressed from a DNA sequence present in human chromosome 17p13.3, said DNA sequence including locus D1728, disruption of said DNA sequence being associated with malimnant cell growth.

* * * * *